United States Patent
Murai et al.

(10) Patent No.: US 11,006,904 B2
(45) Date of Patent: May 18, 2021

(54) PATIENT STATUS NOTIFICATION DEVICE, NOTIFICATION METHOD IN PATIENT STATUS NOTIFICATION DEVICE AND PROGRAM

(71) Applicant: PARAMOUNT BED CO., LTD., Tokyo (JP)

(72) Inventors: Shinya Murai, Tokyo (JP); Jun Tomikawa, Tokyo (JP); Sota Nishiura, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 0 days.

(21) Appl. No.: 16/781,190

(22) Filed: Feb. 4, 2020

(65) Prior Publication Data
US 2020/0170584 A1 Jun. 4, 2020

Related U.S. Application Data

(63) Continuation of application No. 16/217,685, filed on Dec. 12, 2018, now Pat. No. 10,595,793, which is a (Continued)

(30) Foreign Application Priority Data

Jul. 10, 2015 (JP) .................................. 2015-139209

(51) Int. Cl.
*A61B 5/02* (2006.01)
*A61B 5/00* (2006.01)
(Continued)

(52) U.S. Cl.
CPC ................ *A61B 5/746* (2013.01); *A61B 5/00* (2013.01); *A61B 5/0002* (2013.01); *A61B 5/002* (2013.01);
(Continued)

(58) Field of Classification Search
CPC . G06F 19/3418; G08B 21/02; G08B 21/0211; G08B 21/0446; G08B 21/0453;
(Continued)

(56) References Cited

U.S. PATENT DOCUMENTS 5,319,355 A 6/1994 Russek
5,772,586 A 6/1998 Heinonen et al.
(Continued)

FOREIGN PATENT DOCUMENTS

JP 2002-143100 A 5/2002
JP 2004-005341 A 1/2004
(Continued)

*Primary Examiner* — Andrew W Bee
(74) *Attorney, Agent, or Firm* — Birch, Stewart, Kolasch & Birch, LLP

(57) ABSTRACT

For each biological information, a caution level range and a warning level range as to the biological information value are stored. When the acquired biological information value of the biological information of a patient falls within the caution level range, a notice of the status of the patient is given to a first notice destination. When the aforementioned biological information value falls within the warning level range, the notice of the status of the patient is given to a second notice destination. Thus, by switching the notice destinations based on the status of the patient, it is possible to provide a patient status notification device or the like that can appropriately and promptly perform notification.

12 Claims, 28 Drawing Sheets

Related U.S. Application Data continuation of application No. 15/743,600, filed as application No. PCT/JP2016/070263 on Jul. 8, 2016, now Pat. No. 10,188,354.

(51) Int. Cl.

| | | |
|---|---|---|
| G08B 21/02 | (2006.01) | |
| G08B 21/04 | (2006.01) | |
| A61B 5/024 | (2006.01) | |
| A61B 5/145 | (2006.01) | |
| A61B 5/0205 | (2006.01) | |
| A61B 5/01 | (2006.01) | |
| A61B 5/08 | (2006.01) | |
| G16H 50/20 | (2018.01) | |
| G16H 40/67 | (2018.01) | |
| G16H 80/00 | (2018.01) | |
| G16H 15/00 | (2018.01) | |
| G16H 10/60 | (2018.01) | |
| A61B 5/021 | (2006.01) | |

(52) U.S. Cl.
CPC .......... *A61B 5/0008* (2013.01); *A61B 5/0022* (2013.01); *A61B 5/0024* (2013.01); *A61B 5/01* (2013.01); *A61B 5/02* (2013.01); *A61B 5/021* (2013.01); *A61B 5/024* (2013.01); *A61B 5/0205* (2013.01); *A61B 5/02055* (2013.01); *A61B 5/0816* (2013.01); *A61B 5/145* (2013.01); *A61B 5/14532* (2013.01); *A61B 5/14542* (2013.01); *A61B 5/6892* (2013.01); *A61B 5/7282* (2013.01); *A61B 5/7435* (2013.01); *G08B 21/02* (2013.01); *G08B 21/0211* (2013.01); *G08B 21/0446* (2013.01); *G08B 21/0453* (2013.01); *G16H 10/60* (2018.01); *G16H 15/00* (2018.01); *G16H 40/67* (2018.01); *G16H 50/20* (2018.01); *G16H 80/00* (2018.01)

(58) Field of Classification Search
CPC ... A61B 5/0002; A61B 5/0008; A61B 5/0022; A61B 5/02; A61B 5/0205; A61B 5/02055; A61B 5/024; A61B 5/0024; A61B 5/145; A61B 5/14532; A61B 5/7282; A61B 5/00; A61B 5/01; A61B 5/021; A61B 5/0816; A61B 5/32; A61B 5/14542; A61B 5/6892; A61B 5/7435; A61B 5/746; G16H 40/67; G16H 80/00; G16H 15/00; G16H 10/60; G16H 50/20

See application file for complete search history.

(56) References Cited

U.S. PATENT DOCUMENTS

| | | |
|---|---|---|
| 8,092,386 B1 | 1/2012 | Wenzel et al. |
| 8,525,680 B2 | 9/2013 | Riley et al. |
| 2011/0133936 A1* | 6/2011 | Sanchez ............ A61M 16/0051 340/573.1 |
| 2012/0220835 A1 | 8/2012 | Chung |
| 2012/0290311 A1 | 11/2012 | Tara et al. |
| 2013/0267791 A1 | 10/2013 | Halperin et al. |
| 2014/0032238 A1 | 1/2014 | Piao et al. |
| 2014/0198203 A1 | 7/2014 | Vardi et al. |
| 2015/0035675 A1 | 2/2015 | Gunaratnam et al. |
| 2015/0257716 A1 | 9/2015 | Humphrys et al. |
| 2015/0269827 A1 | 9/2015 | Hopkins et al. |
| 2016/0157789 A1 | 6/2016 | Nicolaus |

FOREIGN PATENT DOCUMENTS

| | | |
|---|---|---|
| JP | 2006-060412 A | 3/2006 |
| JP | 2007-020971 A | 2/2007 |
| JP | 2008-501426 A | 1/2008 |
| JP | 2008-167899 A | 7/2008 |
| JP | 2008-531209 A | 8/2008 |
| JP | 2010-022520 A | 2/2010 |
| JP | 2011-147493 A | 8/2011 |
| JP | 2013-169438 A | 9/2013 |
| JP | 2014-510603 A | 5/2014 |
| JP | 2014-124323 A | 7/2014 |
| JP | 2015-058030 A | 3/2015 |

\* cited by examiner

FIG. 5

| Measurement Date | Pulse Rate | Body Temperature | Respiratory Rate | SpO2 |
|---|---|---|---|---|
| 2015/05/16 20:00 | 126 | 37.2 | 15 | 99 |
| 2015/05/16 20:05 | 128 | 37.2 | 13 | 97 |
| 2015/05/16 20:10 | 128 | 37.8 | 16 | 98 |
| ⋮ | ⋮ | ⋮ | ⋮ | ⋮ |

FIG. 6

| Reception Date | Body Temperature | Highest Blood Pressure | Lowest Blood Pressure |
|---|---|---|---|
| 2015/05/16 20:00 | 37.2 | 159 | 98 |
| 2015/05/16 22:00 | 38.0 | 162 | 102 |
| ⋮ | ⋮ | ⋮ | ⋮ |

FIG. 7

| Biological Information | Upper Limit Threshold | | Lower Limit Threshold | |
|---|---|---|---|---|
| | Caution | Warning | Caution | Warning |
| Pulse Rate | 110 | 130 | 60 | 30 |
| Respiration | 30 | 34 | 10 | 8 |
| SpO2 | – | – | 92 | 89 |
| ⋮ | ⋮ | ⋮ | ⋮ | ⋮ |

| Patient No. | Type | Notice Setting |
|---|---|---|
| 100012 | Leaving Bed | OFF |
|  | Respiration | Caution |
|  | Pulse | Warning |
|  | ⋮ | ⋮ |
| ⋮ | ⋮ | ⋮ |

| 1st Notice Destination | Nurse in Charge, PC |
|---|---|
| 2nd Notice Destination | Nurse in Charge, PC, Doctor in Charge |

FIG. 25

Patient Information

Ms. Hanako Tanaka born on Oct. 10, 1986 (age: 28)   2015/05/16 22:26

Basic Information
Medical Care Information
Caution Information
Pictogram

| Patient ID | 0002341237 |
| Patient Last Name | Tanaka |
| Patient First Name | Hanako |
| Gender | Female |
| Blood Type | A |
| Blood Type (Rh) | Rh+ |
| Date of birth | 1986/10/10 |
| Disease Name | |

W700

PATIENT STATUS NOTIFICATION DEVICE, NOTIFICATION METHOD IN PATIENT STATUS NOTIFICATION DEVICE AND PROGRAM

CROSS-REFERENCE TO RELATED APPLICATIONS

This application is a Continuation of co-pending U.S. patent application Ser. No. 16/217,685, filed on Dec. 12, 2018, which is a Continuation of co-pending U.S. patent application Ser. No. 15/743,600 filed on Jan. 10, 2018 (now U.S. Pat. No. 10,188,354 issued on Jan. 29, 2019), which was filed as PCT International Application No. PCT/JP2016/070263 on Jul. 8, 2016, which claims the benefit under 35 U.S.C. § 119(a) to Patent Application No. 2015-139209, filed in Japan on Jul. 10, 2015, all of which are hereby expressly incorporated by reference into the present application.

TECHNICAL FIELD

The present invention relates to a patient status notification device to which a plurality of terminal devices can be connected.

BACKGROUND ART

Conventionally, technologies for giving a notice or an alarm to other terminal devices and the like have been known. For example, there has been disclosed an invention that easily and quickly identifies an alarm output source even under a condition where a plurality of monitoring devices of the same model are installed (e.g., see Patent Document 1).

There also has been disclosed an invention of a nurse call system that allows easy calling from a nurse call parent machine to a portable terminal of a nurse in charge and that enables easy calling to a particular group of a plurality of patients (see, for example, Patent Document 2).

PRIOR ART DOCUMENTS

Patent Documents

Patent Document 1: Japanese Patent Application Laid-open No. 2014-124323
Patent Document 2: Japanese Patent Application Laid-open No. 2006-60412

SUMMARY OF THE INVENTION

Problem to be Solved by the Invention

In practical medical sites and caregiving sites, there are needs for giving notice to an unusual notice destination depending on the condition of the patient and/or the matter to be notified. However, conventionally, the notice destination has been determined in advance, and it has been impossible to change the notice destination depending on the patient's condition or the like.

For example, in the above-mentioned Patent Document 2, since a nurse who has been associated is called, the notification is given to medical staff who should deal with it. However, the notice destination does not change depending on the condition of the patient. Therefore, it is necessary for the recipient of the notice to judge the situation and again to notify or search for the medical staff member who should respond, based on the content of the notified matters, so it has been impossible to make a prompt response.

In view of the above-described problems, it is an object of the present invention to provide a patient status notification device and the like capable of appropriately and promptly notifying by changing a notice destination based on the status of a patient.

Means for Solving the Problem

In order to solve the above-mentioned problems, the patient status notification device of the present invention is a patient status notification device connectable to a plurality of terminal devices, comprising:
a storing means for storing ranges of a caution level and a warning level as to a biological information value for each of biological information;
a biological information acquiring means for acquiring biological information on a patient; and,
a notifying means for giving a notice of a status of the patient, to a first notice destination terminal device when a biological information value of the biological information acquired by the biological information acquiring means falls within in the range of the caution level, and to a second notice destination terminal device when the biological information value falls within in the range of the warning level.

The notification method of the present invention is a notifying method in a patient status notification device connectable to a plurality of terminal devices, comprising:
a storing step of storing ranges of a caution level and a warning level as to a biological information value for each of biological information;
a biological information acquiring step of acquiring biological information on a patient; and,
a notifying step of giving a notice of the status of the patient, to a first notice destination terminal device when the biological information value of the biological information acquired by the biological information acquiring step falls within in the range of the caution level, and to a second notice destination terminal device when the biological information value of the biological information falls within in the range of the warning level.

The program of the present invention is a program for causing a computer connectable to a plurality of terminal devices, to execute:
a storing function of storing ranges of a caution level and a warning level as to a biological information value for each of biological information;
a biological information acquiring function of acquiring biological information on a patient; and,
a notifying function of giving a notice of a status of the patient, to a first notice destination terminal device when the biological information value of the biological information acquired by the biological information acquiring function falls within in the range of caution level, and to a second notice destination terminal device when the biological information value falls within in the range of the warning level.

Advantages of the Invention

According to the present invention, biological information of the patient is acquired, and when the biological information value of the acquired biological information falls within the caution level range, the notice of the status of the patient is given to the first notice destination terminal device. When the biological information value falls within the warning level range, the notice of the status of the patient is given to the second notice destination terminal device. Thus, this configuration enables the notification to an appropriate notice destination based on the patient's condition.

BRIEF DESCRIPTION OF DRAWINGS

FIG. 5 illustrates a diagram for explaining continuous biological information in the present embodiment.

FIG. 6 illustrates a diagram for explaining measured biological information in the present embodiment.

FIG. 7 illustrates a diagram for explaining an alarm threshold table in the present embodiment.

FIG. 25 illustrates a diagram for explaining a screen example as the operation example in the present embodiment.

MODE FOR CARRYING OUT THE INVENTION

Hereinafter, the best mode for carrying out the present invention will be described with reference to the drawings. The following embodiment is an example in which the patient status notification device of the present invention is applied, and it goes without saying that the content of the invention is not limited to the present embodiment.

1. Entire System

Figure 1:
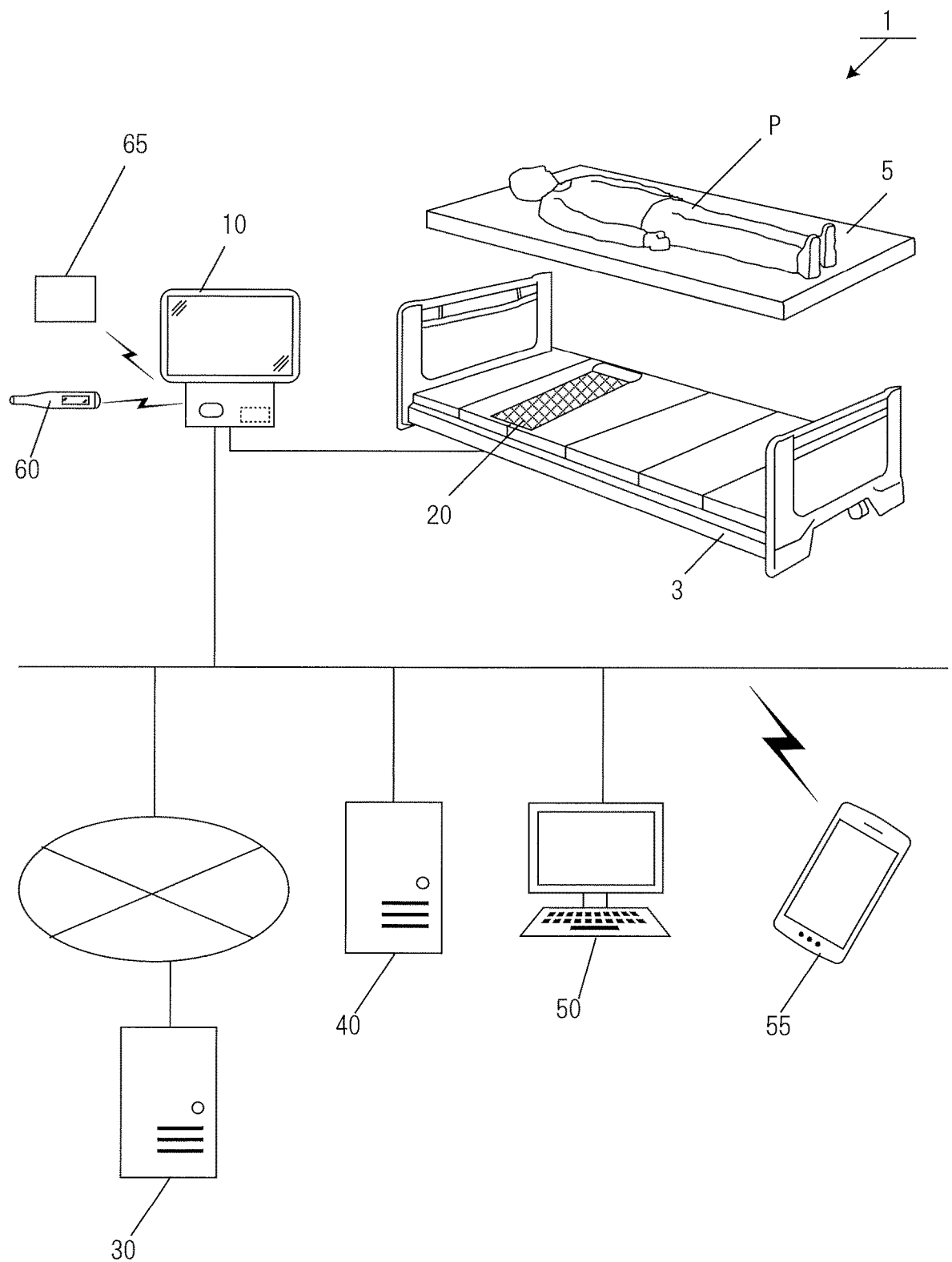
FIG. 1 illustrates a diagram for explaining the entire system in a present embodiment.

To being with, the entire system in this embodiment will be described. FIG. 1 is a diagram for explaining the whole of a patient status notification system 1 incorporating a patient status notification device. First, a patient P lies on a mattress 5 placed on a bed 3. A state detection device 20 is provided in the bed.

The state detection device 20 is a device capable of continuously acquiring biological information of a patient, and acquires values such as a patient's body weight, body movement, blood pressure, and blood glucose level, for example. As an example, the state detection device 20 may be provided, as shown in FIG. 1, between the bed 3 and the mattress 5, or a sensor may be attached to the patient to detect a state thereof. Alternatively, the device may be set directly on the bed device (e.g., a load acting on an actuator is used). Then, the state detection device 20 is connected to the patient status display device 10.

The patient status display device 10 has a function of a patient status notification device and is connected to the state detection device 20, connected to a measuring device 60, and/or connected to another server device or the like via a network. Further, by placing an authentication card 65 over the patient status display device 10, authentication processing (login processing) can be performed.

The login process is a process that is performed by an authorized person such as a staff (nurse, doctor, assistant staff), or the like. By logging in, the person can check the biological information values and the content of the alarm and register them into the electronic medical record. It is possible to set authority for each log-in person so as to differentiate the operable range.

Connected to the network are, for example a server 30, an electronic medical record server 40, a terminal device 50 and a portable terminal device 55 are connected to the network.

The server 30 is a server that provides various services, and may be connected to a LAN in the hospital or facility, or may be provided externally via the internet.

The electronic medical record server 40 is a server that stores information of electronic medical records on patients. Usually, this server is connected to the network in the hospital or facility, but for example, an external cloud server may be used.

The terminal device 50 is a terminal device allowing connection in a nurse station or a management room and enables a grasp of the state of the patient status display device 10 from a remote place. Further, the portable terminal device 55 can be wirelessly connected to a LAN, for example, so that a nurse, assistant staff and the like can easily check information of the patient status display device 10.

As will be described later, the terminal device 50 and the portable terminal device 55 are notified depending on the patient's condition. The notification may be given directly from the patient status display device 10 or may be given notice via the server 30.

Figure 2:
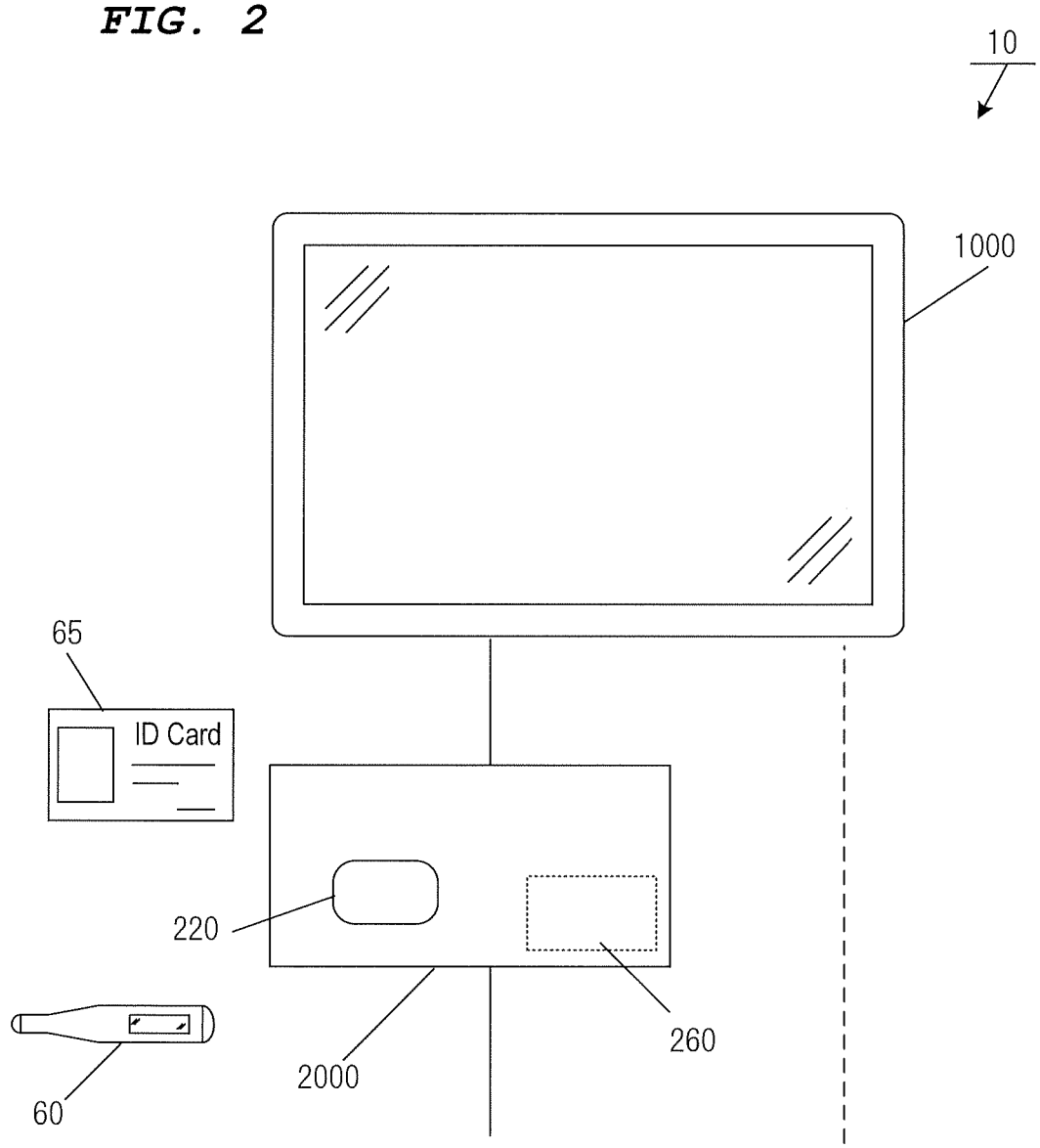
FIG. 2 illustrates a diagram for explaining a patient status display device according to the present embodiment.

The patient condition display device 10 will be described in detail with reference to FIG. 2. The patient status display device 10 includes a display terminal 1000 and a connection device 2000. The display terminal 1000 is, for example, a tablet type display terminal and displays various types of information and receives inputs of various operations. The display terminal 1000 may be a dedicated terminal as a part of the patient status display device 10, or may be implemented by installing application (program) in a general-purpose tablet terminal.

The connection device 2000 is a device for connecting the display terminal 1000 to various devices. That is, this device functions like a hub for various devices. For example, as shown in FIG. 1, connection of this device to the state detection device 20 makes it possible to continuously acquire the biological information of the patient, receive biological information from the measuring device 60 (e.g., a thermometer) and also receive biological information from a device attached to the patient's body (e.g., a wristwatch type wearable measuring device). Further, when the authentication card 65 is made to access a communicator 220, for example, it is also possible to perform an authentication process (e.g., patient authentication and staff authentication). As an authentication method, NFC is used as an example of short-range wireless communication in the present embodiment, but it is also possible to use other methods such as barcode, infrared, IC tag.

Further, a notifying unit 260 is provided so as to be able to give notice when, for example, an error occurs. Furthermore, the notifying unit is connectable to a server device and the like via a LAN (LAN may be either a wired LAN or a wireless LAN). The notifying unit 260 may be configured to be invisible in the normal condition and lit (displayed) only when giving notice. Further, the notifying unit may be configured to give notice by sound such as an alarm sound, warning sound and voice, or by light, instead of display.

In this embodiment, the display terminal 1000 is described as being used by being mounted on the connection device 2000, but the display terminal 1000 and the connection device 2000 may be used separately. For example, the display terminal 1000 may be taken out and used in another place, or the connection device 2000 may be built in the bed device while the display terminal 1000 may be used separately.

2. Functional Configuration

Figure 3:
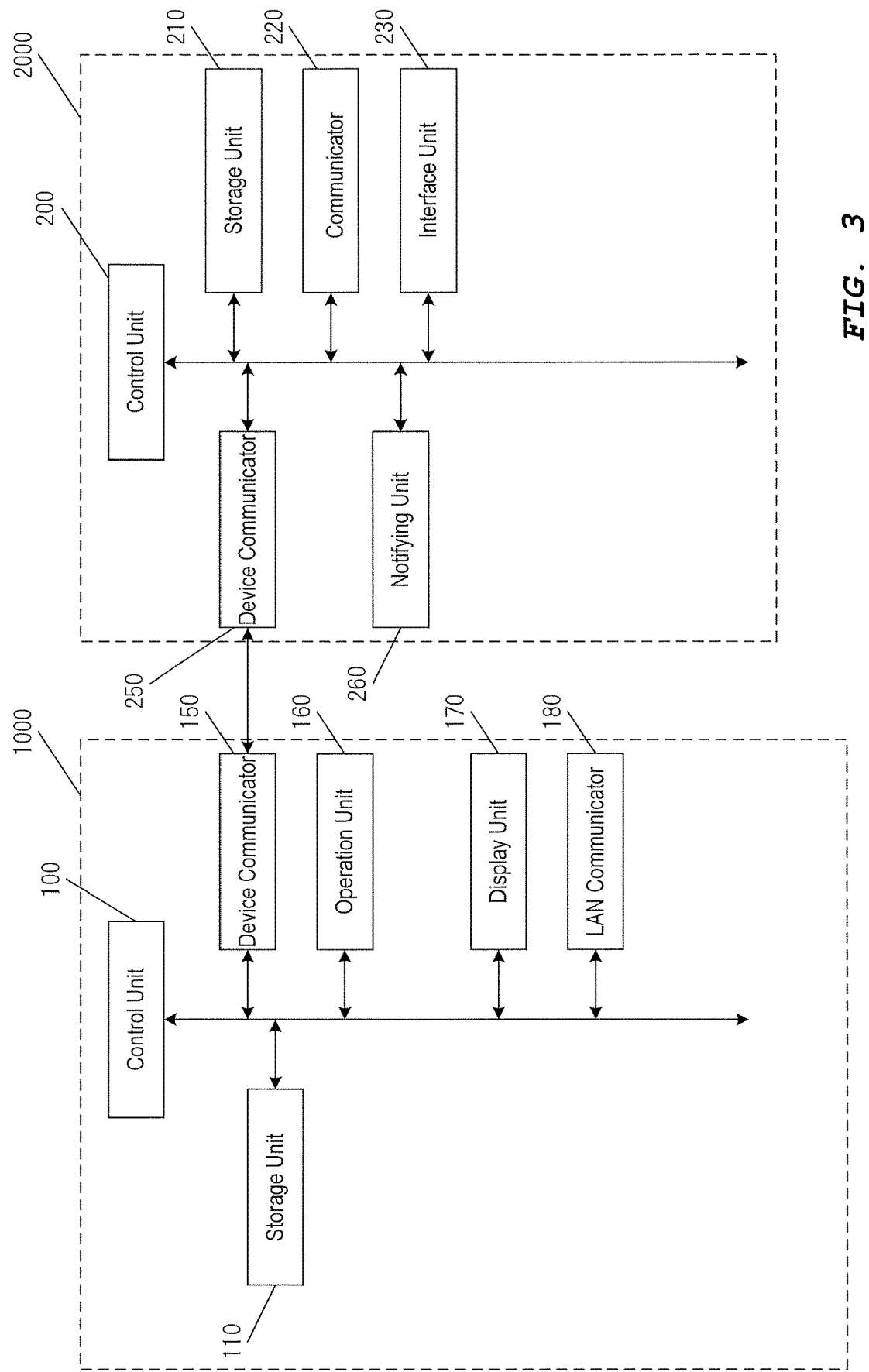
FIG. 3 illustrates a diagram for explaining a functional configuration of a display terminal and a connection device in the present embodiment.

Next, the functional configuration in the present embodiment will be described with reference to the drawings. FIG. 3 is the diagram for explaining the functional configurations of the display terminal 1000 and the connection device 2000 in the patient status display device 10.

[2.1 Display Terminal]

First, the functional configuration of the display terminal 1000 will be described. The display terminal 1000 includes a control unit 100, a storage unit 110, a device communicator 150, an operation unit 160, a display unit 170 and a LAN communicator 180.

The control unit 100 is a functional unit for controlling the entire display terminal 1000. The control unit 100 realizes various functions by reading and executing various programs stored in the storage unit 110 and is configured by, for example, a CPU (Central Process Unit) or the like.

The storage unit 110 is a functional unit in which various programs necessary for the operation of the display terminal 1000 and various data are stored. The storage unit 110 is composed of, for example, a semiconductor memory, an HDD (Hard Disk Drive) or the like.

Figure 4:
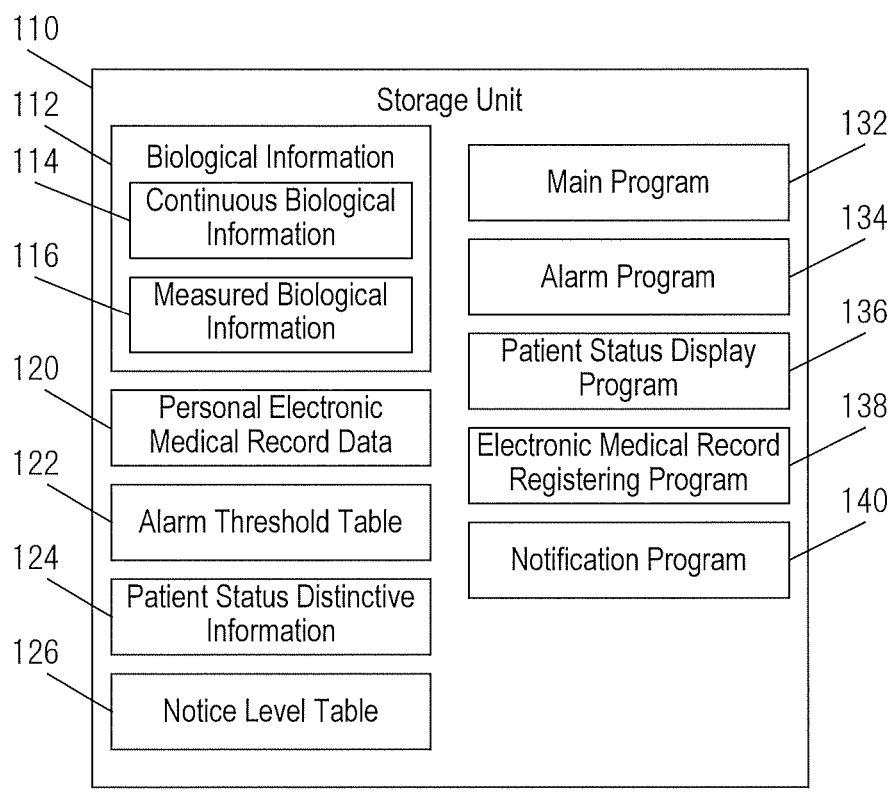
FIG. 4 illustrates a diagram for explaining a storage unit in the present embodiment.

Here, the configuration of the storage unit 110 will be described with reference to FIG. 4. The storage unit 110 stores biological information 112, personal electronic medical record data 120, an alarm threshold table 122, patient status distinctive information 124 and a notice level table 126, and also stores as programs, a main program 132, an alarm program 134, a patient status display program 136, an electronic medical record registering program 138 and a notification program 140.

Stored as the biological information 112 are continuous biological information 114 which is biological information continuously detected from the state detection device 20 and measured biological information 116 which is received from the measuring device 60 at an arbitrary point of time. Here, as the measured biological information, it is also possible to use manual input and/or the values of the continuous biological information instead, if required.

FIG. 5 shows an example of a data structure of the continuous biological information 114. Stored as the continuous biological information 114 of the present embodiment are the values of the biological information detected from the state detection device 20 and state values of biological information that can be detected from the other patient.

That is, the information is stored based on continuously detectable values. The stored examples include the measurement date and time (e.g., "2015/05/16 20:00") and values of certain types of biological information such as the pulse rate (e.g., "126") and the body temperature (e.g., "37.2"), the breathing rate (e.g., "15") and SpO2 (e.g., "99"). That is, the continuous biological information 114 can obtain the predetermined measurement values at any time. The continuous biological information 114 may be acquired from the state detection device 20 or may be acquired from detection devices provided in the bed 3. Alternatively, various sensors may be provided on the body of the patient to acquire the information.

The thus acquired various types of biological information can be collectively managed as continuous biological information. Various values of biological information are detected as required (e.g., when a body motion detection sensor alone is used, body movement state, sleeping state, patient posture (away from bed, in bed, sitting in bed), pulse rate and respiratory rate are detected as continuous biological information).

Stored as the measured biological information 116 is biological information received from external measuring devices such as a thermometer, a blood pressure monitor, a body fat meter and the like. As shown in FIG. 6, examples of the measured biological information 116 of the present embodiment may include the reception date and time (e.g., "2015/05/16 20:00") and values for individual types of biological information (e.g., "37.2" for "body temperature"). Also, for example, the highest blood pressure (e.g., "159") and the lowest blood pressure (e.g., "98") may be stored.

The detected continuous biological information 114 and measured biological information 116 may be stored for a predetermined period of time. For example, as to the period for storing data, data for one day or three days may be stored. Further, the continuous biological information 114 and the measured biological information 116 may be stored in the server 30.

The personal electronic medical record data 120 stores electronic patient record data of an individual patient. The collection of the patient's individual electronic medical record data is stored in the electronic medical record server 40. Since the data structure of the personal electronic medical record data 120 is the same as that stored in the electronic medical record server 40, details will be described later. Briefly, other than patient information, continuous biological information, measured biological information and the like at the time of registration are registered.

Though the present embodiment is described on the assumption that the electronic medical record is stored in the storage unit 110, data from the electronic medical record server 40 may be directly used. In this case, it is not necessary to store the personal electronic medical record data 120 in the storage unit 110.

The alarm threshold table 122 stores alarm thresholds for various biological information values. When the value of the measured (received) biological information exceeds the alarm threshold, notice is given and/or error processing is performed. This alarm threshold may be set in advance or set arbitrarily.

FIG. 7 shows an example of the alarm threshold table 122. As shown in FIG. 7, upper and lower alarm thresholds are stored for each type of biological information. In addition, a plurality of alarm thresholds can be stored for different alarm levels. In the present embodiment, two alarm level ranges, i.e., a caution level range and a warning level range are specified by the alarm thresholds and stored.

For example, as to "pulse" which is one of the biological information, thresholds (threshold values specifying the ranges of caution and warning levels) of the pulse rate as the biological information value are stored. As the upper limit threshold, "110" is stored for the caution level and "130" is stored for the warning level. On the other hand, as the lower threshold, "60" is stored for the caution level and "30" is stored for the warning level.

For example, when being equal or higher than 130, or equal to or lower than 30, the pulse rate can be determined to fall in the warning level range. Also, when being "equal to 110 or higher than 110 and lower than 130" or "higher than 30 and lower than 60 or equal to 60", the pulse rate can be determined to fall in the caution level range. Each range may also be specified to start beyond the threshold (for example, the warning level range of the pulse may be specified to be higher than 130 or lower than 30).

Though, in the present embodiment, for description convenience, an example defined with two ranges, i.e., the caution level range and the warning level range is given, it is a matter of course that two or more level ranges may be set up.

The patient status distinctive information 124 is information for storing the status of the patient. The patient status distinctive information is used to perform patient status distinctive display, which will be described later. In the present embodiment, the patient status distinctive information determined based on the biological information of the patient in the interval from logout to the present (interval patient status distinctive information) and the patient status distinctive information determined based on the current biological information of the patient (current patient status distinctive information) are stored.

Here, as the patient status distinctive information, "normal", "caution" or "warning" state is stored. Normal refers to a case where the biological information values of the patient fall within the alarm threshold range (a range that is neither the caution level nor the warning level). "Caution" is a case where among the biological information values of the patient, there is a biological information value falling within the threshold range of the caution level. Likewise, "warning" is a case where among the biological information values of the patient, there is a biological information value falling within the threshold range of the warning level.

In the present embodiment, the interval patient status distinctive information is determined based on the biological information values at the time of the last logout, but may be determined, for example, at the last login. Further, another piece of interval patient status distinctive information may be additionally stored based on the biological information values between the logout at the time before last and the last login time.

Here, in the present embodiment, the patient status distinctive information changes if one of the biological information values falls within the associated range. However, the patient status distinctive information may be updated when a plurality of biological information values fall in the caution level or warning level. Further, the patient status distinctive information is not limited single one, the patient status distinctive information may be stored individual biological information or individual predetermined group of biological information. For example, the continuous biological information and the measured biological information are classified into different predetermined groups, so that the patient status distinctive information may be determined based on the individual patient condition and stored separately.

Figures 8, 9, 10:
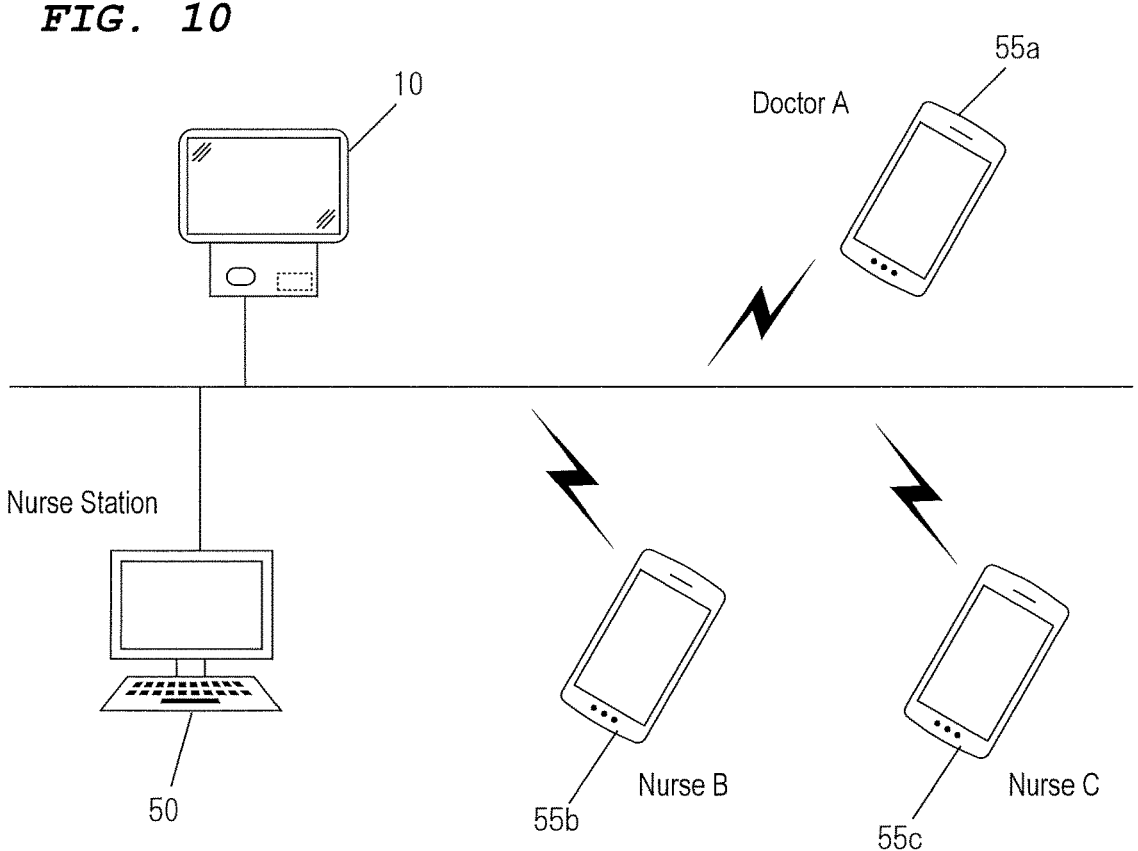
FIG. 8 illustrates a diagram for explaining a notice level table in the present embodiment.
FIG. 9 illustrates a diagram showing one example of notice destinations in the present embodiment.
FIG. 10 illustrates a diagram for explaining the entire system of notification in the present embodiment.

The notice level table 126 is a table for storing how notice should be given for each patient in association with the condition of the patient and each type of biological information. For example, as shown in FIG. 8, in association with a patient number, a type (e.g., "breathing") and a notice setting (e.g., "caution") indicating whether it is necessary to notify based on the associated biological information, are stored.

As the notice setting, "OFF" for no notice, "caution" for giving notice when in the caution level as a notification level and "warning" for giving notice when in the warning level are stored. Also, for some types of information such as information on whether or not the patient is leaving bed, simply "ON" or "OFF" may be set.

Further, the notice destinations are previously determined in association with the notice setting. For example, as shown in FIG. 9, as the first notice destination, the "nurse in charge" and "PC" at the nurse station etc., are designated. Also, as the second notice destination, the "doctor in charge" in addition to the "nurse in charge" and "PC" is designated.

In this case, when the notice setting is "ON" or "caution", notice is given to the first notice destination. When the notice setting is "warning", notice is given to the second notice destination. Further, in the present embodiment, the "nurse in charge" and the "doctor in charge" are extracted from the electronic medical record. Note that the notice destination information may be set separately from the electronic medical record.

Now, the notification operation will be described with reference to FIG. 10. Description will be made on a case where, for example, the doctor in charge of a patient is a doctor A and the nurse in charge of the patient is a nurse B.

When notice in the caution level for the patient is given by the patient status display device 10, a notification is made to the terminal device 50 in the nurse station and the portable terminal device 55b. In this case, no notification is given to the doctor A's portable terminal device 55a and the nurse C's portable terminal device 55c.

When notice in the warning level for the patient is given, a notification is sent to the doctor A's portable terminal device 55a in addition to the terminal device 50 and the portable terminal device 55b. In this case, no notification is made to the nurse C's portable terminal device 55c.

In this manner, depending on the content according to the notice setting, notification is made to the previously set notice destination. Though, in the present embodiment, the notice destinations are set for each patient, a common notice destination may be set. For example, suppose that a rapid response team is set up as an emergency notice destination for all patients. In this case, it is possible to provide a configuration in which when, for example, a biological information value of the patient exceeds its emergency threshold, or when a plurality of warning level states take place, a notification to the emergency notice destination is made.

Here, the notice setting is configured such that a notification is given in the case of a caution level or warning level, which means that the notification is given in excess of each level. For example, when the notice setting is set at the caution level, the notification is given to the first notice destination when the associated biological information reaches the caution level, and notification is given to the second notice destination when the warning level is reached. That is, the notice setting of the caution level contains that of the warning level. It is possible to configure the notice setting such that the notification is made based on caution level alone.

The programs stored in the storage unit 110 can be read out by the control unit 100, which realizes various functions. More specifically, reading and execution of the main program 132 implements a main function, reading and execution of the alarm program 134 implements an alarm function, reading and execution of the patient status display program 136 implements a patient status display function, reading and execution of the electronic medical record registering program 138 implements an electronic medical record registering function, and reading and execution of the notification program 140 implements a notification function.

The device communicator 150 is a functional unit for communicating with a device communicator 250 to be described later. Though in description of the present embodiment, communication is performed by USB connection, other versatile connection methods, wireless connection (Bluetooth (registered trademark), wireless LAN, etc.) may be used. Alternatively, a dedicated connection interface may be provided to perform communication.

The operation unit 160 is a functional unit that receives operation input from a user, and may be formed of, for example, software keys realized by a touch panel and/or input devices such as a keyboard, a mouse and the like. Also, voice input and other input methods may be employed.

The display unit 170 is a functional unit that displays various kinds of information to the user and performs notification processes and is realized by means of, for example, a liquid crystal display etc. Further, the operation unit 160 and the display unit 170 may be integrally formed of a touch panel.

The LAN communicator 180 is an interface unit connectable to the LAN, and formed by a NIC for connecting to Ethernet (registered trademark) or the like. The LAN communicator 180 may be provided in the connection device 2000. In this case, the data to be transmitted is once sent to the connection device 2000 via the device communicator 150 (250), and then transmitted to the network. Note that connection to the LAN may be implemented by either wired or wireless one.

[2.2. Connection Device]

Subsequently, the functional configuration of the connection device 2000 will be described. The connection device 2000 includes a control unit 200, a storage unit 210, the communicator 220, an interface unit 230, the device communicator 250 and the notifying unit 260.

The control unit 200 is a functional unit for controlling the connection device 2000 as a whole. The control unit 200 realizes various functions by reading out and executing various programs stored in the storage unit 210 and is configured of, for example, a CPU (Central Process Unit) and the like.

The storage unit 210 is a functional unit in which various programs necessary for the operation of the connection device 2000 and various data are stored. The storage unit 210 is composed of, for example, a semiconductor memory, an HDD (Hard Disk Drive) or the like.

The communicator 220 is a functional unit for communicating with other devices and an authentication card. For example, the communicator can perform NFC (Near Field Communication) communication as short-range communication. In the case of NFC communication, authentication is performed by placing the authentication card 65 thereover. Further, when the measuring device 60 has the NFC communication function, by placing the measuring device 60, it is possible to receive the biological information via the connection device 2000. As the measuring device 60, for example a device such as a smartphone may be used, or a wearable terminal device such as a watch may be used.

As a matter of course, as the communicator 220, any method such as Bluetooth (registered trademark), TransferJet (registered trademark), ZigBee (registered trademark) and RFID may be adopted. Further, a LAN (wireless LAN, wired LAN) or the like may be used.

The interface unit 230 is a functional unit for communicating with other devices. For example, this unit is provided as a functional unit for connection with the state detection device 20. The interface for connection may be implemented by a dedicated interface or may be realized by a general-purpose interface such as USB or RS-232C.

The device communicator 250 is a functional unit for enabling communication between the display terminal 1000 and the connection device 2000 via the aforementioned device communicator 150. Connection for this may be implemented using, for example USB or the like or via a LAN. In the present embodiment, for explanation convenience, the functions of the communicators are described separately from one another, but may be integrated into one. That is, when all the communications are performed by Bluetooth, the device communicator 250, the communicator 220 and the interface unit 230 can be configured by one functional unit.

The notifying unit 260 is a functional unit that operates when the connection device 2000 implements a notification process. For example, if an error display needs to be done, this is done. As a means for notifying, any method such as sound, light, display, vibration, etc. can be considered.

[2.3 Electronic Medical Record Server]

Figure 11:
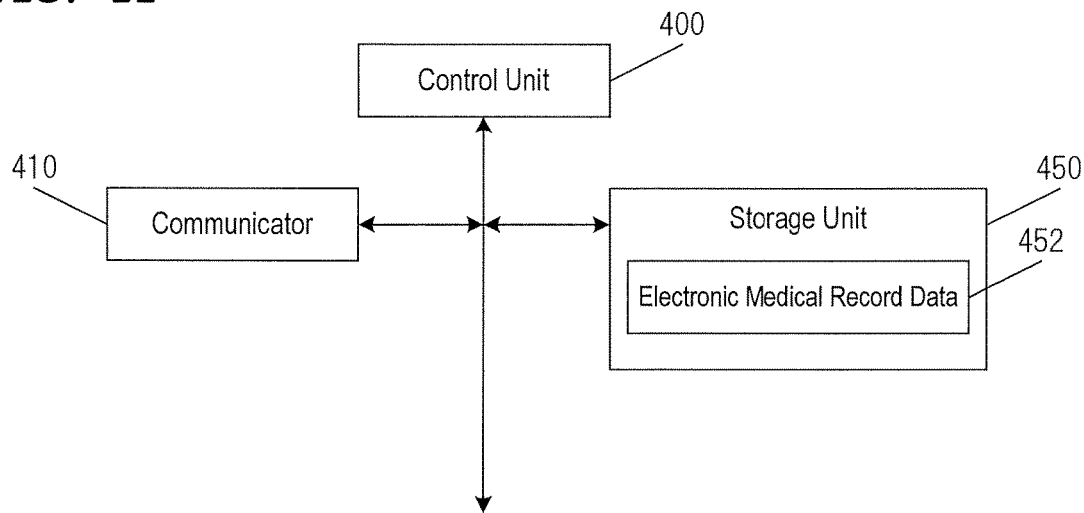
FIG. 11 illustrates a diagram for explaining a functional configuration of an electronic medical record server in the present embodiment.

Next, the functional configuration of the electronic medical record server 40 will be described with reference to FIG. 11. The electronic medical record server 40 includes a control unit 400, a communicator 410 and a storage unit 450.

The control unit 400 is a functional unit for controlling the electronic medical record server 40 as a whole. The control unit 400 realizes various functions by reading out and executing various programs stored in the storage unit 450, and is configured of, for example, a CPU (Central Process Unit) and the like.

The communicator 410 is an interface unit for connection to a network. This unit is composed of, for example, an NIC that can be connected to Ethernet. The communicator 410 enables communication with other devices through itself.

The storage unit 450 is a functional unit in which various programs necessary for the operation of the electronic medical record server 40 and various data are stored. The storage unit 450 is configured of, for example, a semiconductor memory, an HDD (Hard Disk Drive) or the like.

Figure 12:
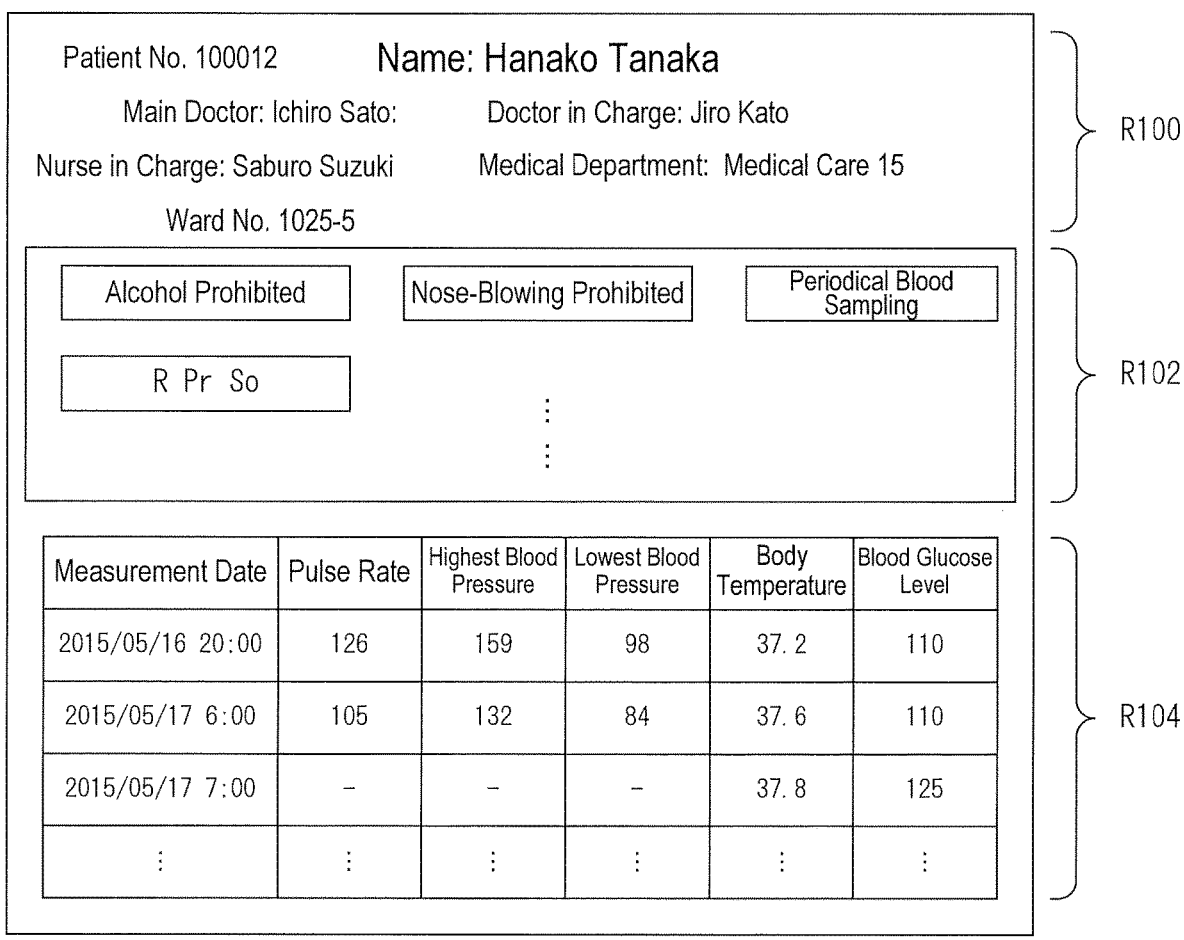
FIG. 12 illustrates a diagram for explaining electronic medical record data in the present embodiment.

Stored in the storage unit 450 is electronic medical record data 452. FIG. 12 shows an example of electronic medical record data. The electronic medical record data stores patient information for each patient, including basic information such as patient number and name, and medical care information such as a doctor in charge as in R100 of FIG. 12 and caution information (R102) indicating a patient's condition and the like, a pictogram, and measured biological information (biological information values) (R104).

Here, the caution information is information for making the medical staff, assistant staff, etc., and experts aware the conditions of the patient. For example, warning information (prohibition of nose blowing etc.) and risk assessments such as bedsore assessment, risk-of-falling assessment etc., are recorded. These information may be controlled by flags or may be managed by text, icons, pictures and others.

In addition, pictogram information may be stored for easier understanding. Pictograms are based on information on everyday life. Display of the pictograms enables a person who happens to pass by to take care of the patient, thereby providing safety and security. In this way, the pictogram information conveys information on the conditions of the patient to be notified to many people, whereas the caution information conveys information on the status of the patient to the experts.

3. Screen (State) Transition Diagram

Next, the flow of the entire system in the present embodiment will be described using the screen transition diagram (state transition diagram) in FIG. 13.

First, when the system is activated, it is determined whether an alarm state is taking place, that is, whether any of biological information values exceeds the alarm threshold (or is less than the alarm threshold). Then, an alarm screen (P100) is displayed as necessary. This alarm screen can tell occurrence of a problem, but will not display the content of the error until the user logs in. This feature makes it possible to prevent display of the content of an error which should not be notified to the patient and family.

Though the alarm screen is displayed when the system is started such as when the power is turned on, occurrence of an alarm state may also be checked at any time. So, the current screen may be interrupted and transitioned to the alarm screen once an alarm state takes place.

Subsequently, a patient status display screen (P102) is displayed as the main state. In this screen, name plate information, pictogram information, caution information, error status and the like are displayed as basic information of the patient. Thereby, it is possible to display necessary information to medical staff such as nurses and doctors, caregivers and families who are taking care of the patient.

The patient status display screen (P102) does not display detailed information because it can be seen by the patient, family members and third parties who visited the hospital. The patient status display screen can be switched into the login screen (P104) as necessary, by executing authentication processing and by performing log-in processing. From the login screen, it is possible to transition to various screens. For example, the login screen can be switched to a patient information display screen (P114) capable of displaying patient information, a biological information display screen (P106) displaying biological information values, a graph display screen (P108) capable of displaying the history of biological information values and a vital registration screen (P110) for registering the biological information values in the electronic medical record.

Furthermore, it is possible to switch to an alarm setting/history screen (P116) for setting conditions to actuate an alarm state and a reminder screen (P112) which can be set for the things to do next (e.g., instruction of medication etc.).

In addition, separately from this screen, a notification process is executed as necessary by interruption. When any of biological information values reaches the caution or warning threshold, a notification process is executed so that notice is given to other devices. At this time, it is possible to configure the system such as to appropriately display the fact that the notice has been made, on each of the screens.

As described above, according to the present embodiment, it is possible to display information relating to the patient in a unified manner and display appropriate information by switching the screens as necessary. Further, by collectively obtaining information from a plurality of measuring devices in a unified manner and registering them in the electronic medical record, it is possible to manage the information on the patient in a unified manner.

4. Explanation of Individual Processes

Next, each process in the present embodiment will be described with reference to the drawings.

[4.1 Main Process]

The main process in this embodiment will be described with reference to FIG. 14. The main process is a process realized by the control unit 100 which reads out and executes the main program 132 stored in the storage unit 110.

First, it is determined whether or not an alarm state is occurring (Step S102). Specifically, each vital value is compared with its alarm threshold so as to determine whether the vital value exceeds the alarm threshold or is less than the alarm threshold and determine whether or not to issue an alarm. If it is necessary to issue the alarm, an alarm process is effected (Step S102; Yes→Step S104 in FIG. 15).

It should be noted that whether or not each vital exceeds the alarm threshold depends on the type of biological information. Besides, there are cases in which judgment is made on both the judgment criteria (that is, it is determined whether or not the vital value is within a predetermined range).

Figure 16:
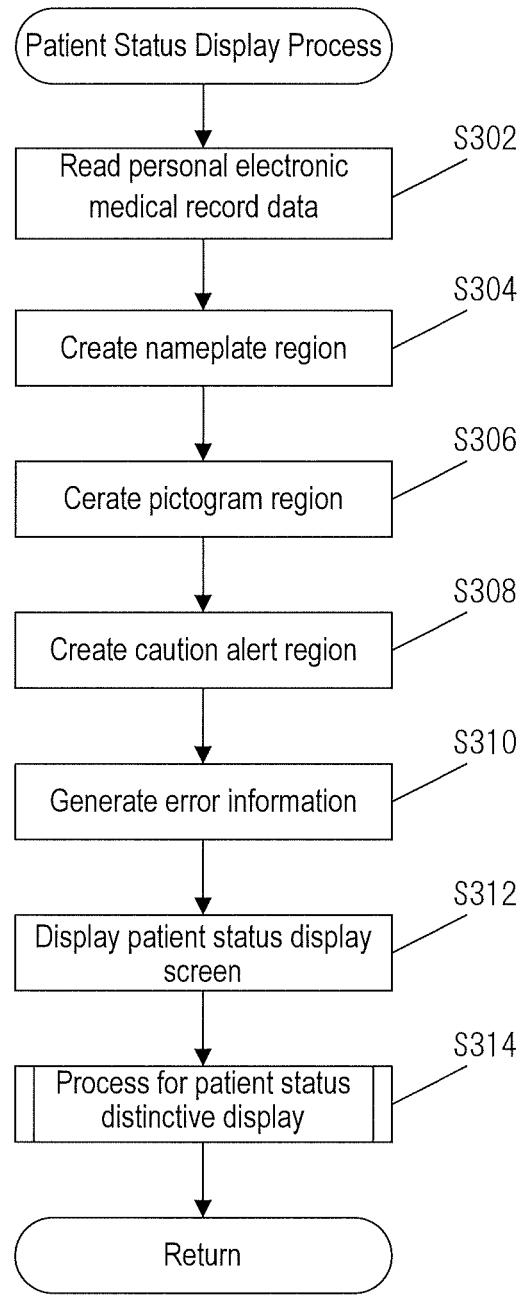
FIG. 16 illustrates a diagram for explaining an operation flow of a patient status display process in the present embodiment.

Subsequently, the patient status is determined, so that a patient status display process for displaying the patient status based on the determined result is executed (Step S106 in FIG. 16). Here, if login authentication is not performed (or login has failed), the control is repeatedly executed from Step S102 (Step S108; No→Step S102).

Here, when the login authentication is performed correctly (Step S108; Yes), a staff screen as the login screen is displayed (Step S110). The staff screen is a screen on which various processes can be selected. Here, when a staff process is selected (Step S112: Yes), processing is executed according to the selected staff process (Step S114). Each of the processes executed here will be described later.

When logout is not performed regardless of the state that the staff process is not selected (Step S112; No) or the staff process has been executed, the login state continues and the same control is repeated (Step S116; No→Step S110). On the other hand, when logout is performed, the user logs out and the process from Step S102 is repeatedly executed (Step S116; Yes→Step S102).

Figure 13:
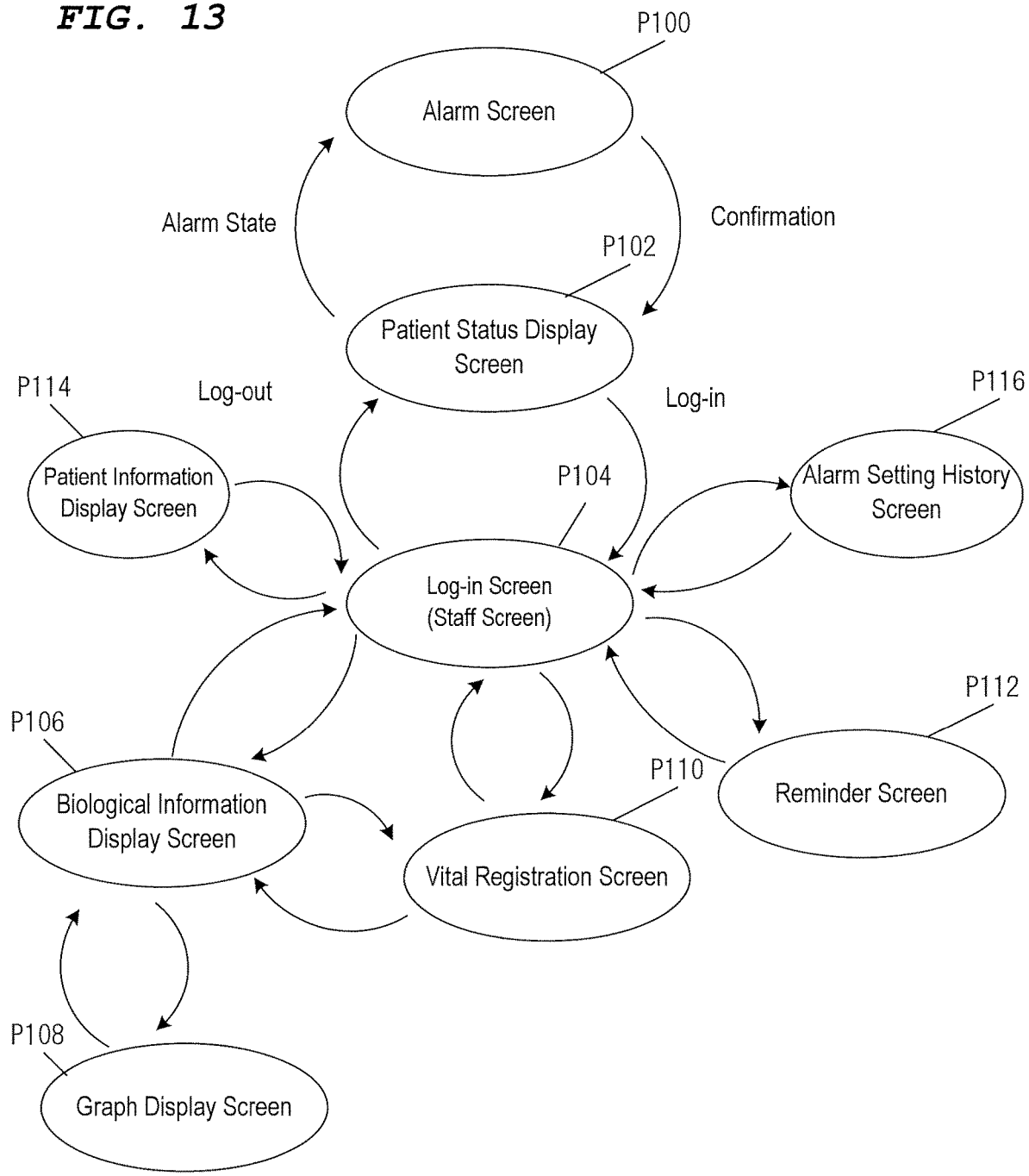
FIG. 13 illustrates a diagram for explaining the overall flow in this embodiment, focusing on screen transitions.

Here, the selected staff process is one of processes corresponding to P106 to P116 illustrated in the screen transition diagram of FIG. 13. These processes will be described using processing flows and/or screen examples.

[4.2 Alarm Process]

Alarm processing will be described with reference to FIG. 15. Alarm processing is a process corresponding to P100 in FIG. 13 (Step S104 in FIG. 14) and is implemented by the control unit 100 which reads out and executes the alarm program 134 stored in the storage unit 110.

First, it is determined whether there is a device connection error (Step S202). Here, if there is a device connection error, a device error output is displayed (Step S202; Yes→Step S204).

Then, it is determined whether there is biological information being in an alarm state (Step S202; No→Step S206, or Step S204→Step S206). Specifically, each biological information value is compared with its alarm threshold so as to determine whether or not the value is in an alarm state. If there is a biological information value that produces the alarm state (Step S206; Yes), a notification process is executed (Step S208).

As an example of the notification process, a notification is given by the notifying unit 260, or an alarm screen is displayed on the display unit 170. At this time, detailed information should be displayed only after logging in (only after being authenticated).

Figure 14:
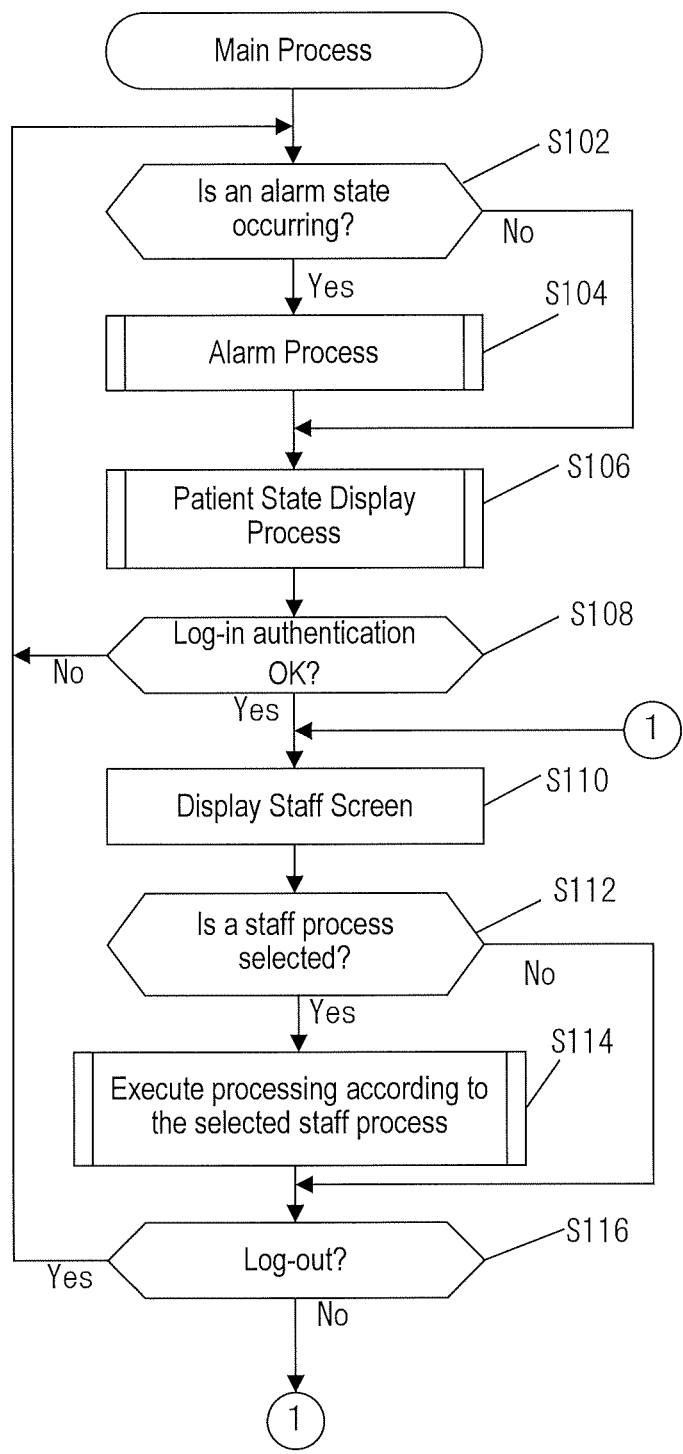
FIG. 14 illustrates a diagram for explaining an operation flow of main processing in the present embodiment.
Figure 15:
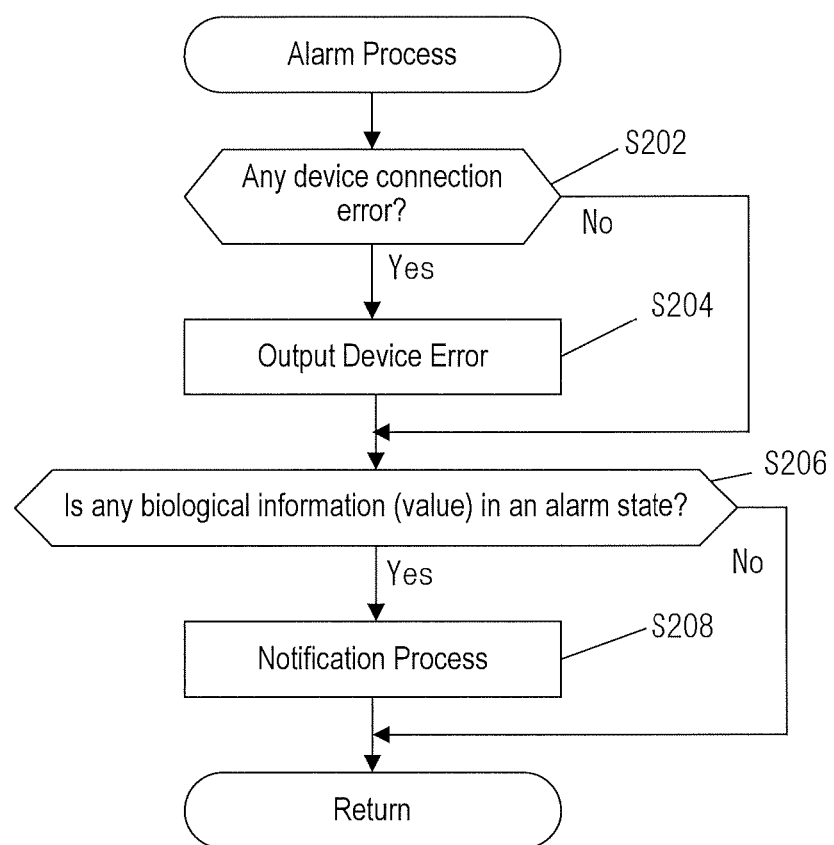
FIG. 15 illustrates a diagram for explaining an operation flow of an alarm process in the present embodiment.

Although the alarm process is described as being executed at Step S104 in FIG. 14, it is possible to configure the system such that the alarm process may be performed as an interrupt process by checking the system at intervals of a predetermined period.

In this way, if there is biological information that produces the alarm state, it is possible to raise the alarm by performing the notification process. In addition, if there occurs the device connection error, the device error may be output as one of alarm processing. It should be noted that the device connection error may be output by another method, or may be made so as not to be output.

[4.3 Patient Status Display Process]

[4.3.1 Processing Flow]

Patient status display processing will be described with reference to FIG. 16. The patient status display processing is a process corresponding to P102 in FIG. 13 (Step S106 in FIG. 14), and is implemented by the control unit 100 which reads out and runs the patient status display program 136 stored in the storage unit 110.

First, the personal electronic medical record data 120 is read out (Step S302). Here, it is possible to provide a configuration such that authentication of the patient is performed before reading out the data of the electronic medical record, then the data on the authenticated patient is read out.

Next, a name plate region is created from the basic information and the medical information contained in the personal electronic medical record data 120 (Step S304), and a pictogram area is further created from the caution information and the set pictogram (Step S306).

Specifically, the name plate region (the region in which name plate information is displayed on the display screen) is created from the basic information contained the name, room number and the name of a doctor in charge, stored in the personal medical record data 120 synchronized with the electronic medical record data 452 of the electronic medical record server 40.

Also, based on general caution information for the patient/carer person, stored in the personal electronic medical record data 120, a display of the pictogram is created.

Subsequently, a warning region based on the caution information is created (Step S308), and if there is error information, error information is generated (Step S310). Herein, the warning information to be displayed in the warning region is created based on information that alerts the experts such as medical staff and carer. Therefore, the region is created in such a manner that those other than the medical staff, such as the patient and their family members, cannot understand the content just looking the display. In addition, the error information contains information relating to the alarm, but similarly the region is created in such a manner that those other than the medical staff, such as the patient and their family members, cannot understand the content just looking the display.

Thus, the patient status display screen is filled with the regions created by the above steps, and displayed (Step S312).

[4.3.2 Patient Status Distinctive Display Process]

Figure 17:
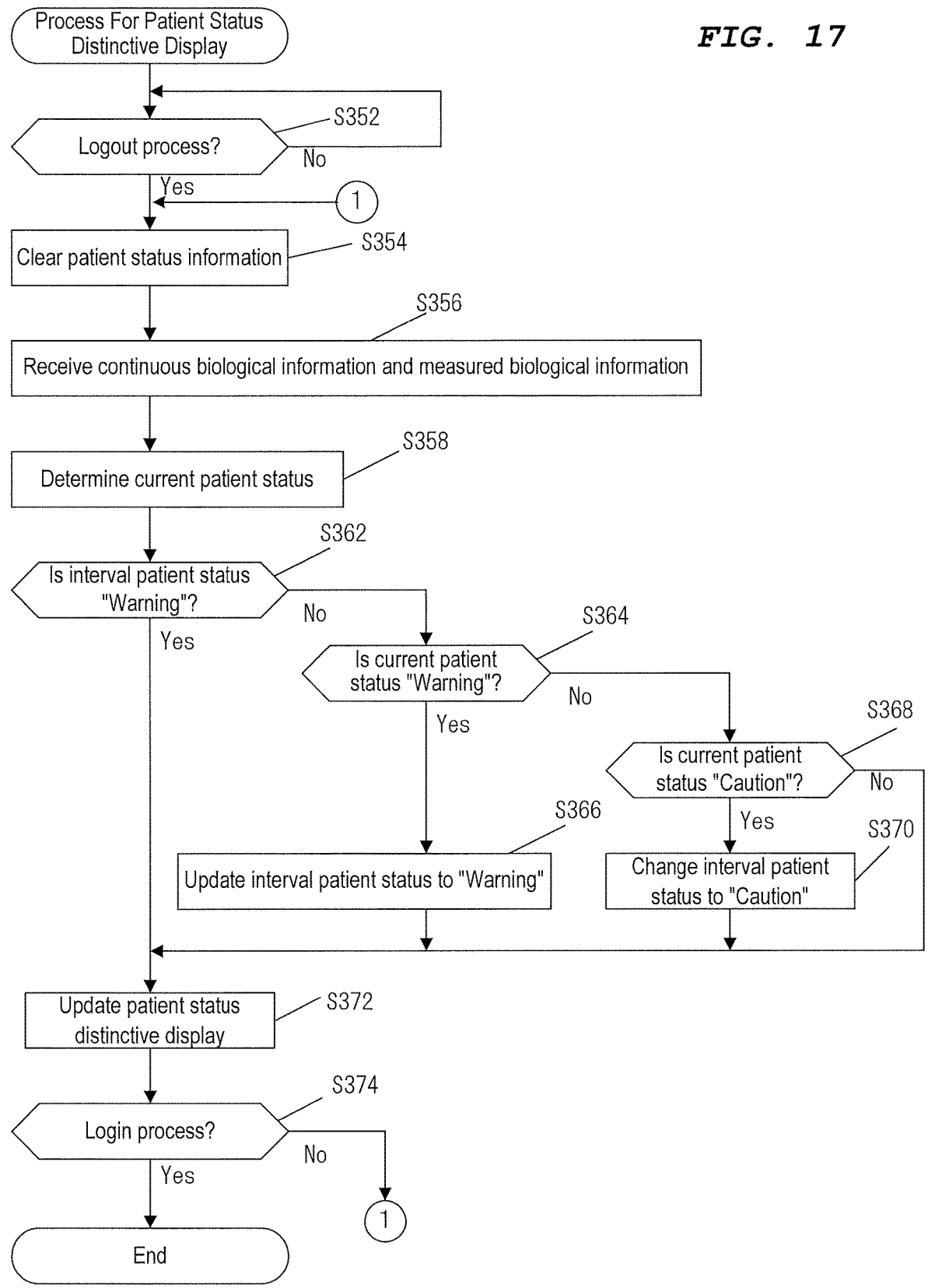
FIG. 17 illustrates a diagram for explaining an operation flow of a patient status distinctive display process in the present embodiment.

Next, patient status distinctive display processing is executed to display the patient status distinctively on the patient status display screen (Step S314). Now, the patient status distinctive display processing will be described with reference to FIG. 17.

First, when a logout process is performed (Step S352; Yes), the currently stored patient status information is once cleared (Step S354). Then, the continuous biological information and the measured biological information are received (input) (Step S356).

When the continuous biological information or the measured biological information is received, the current patient status (current patient status) is determined (Step S358). Here, the current patient status is determined to be in one of "warning", "caution" and "normal" based on all the received biological information. Specifically, the status is determined to be "caution" if any of biological information values is contained in the caution level defined by alarm thresholds, and to be "warning" if any of biological information values is contained in the warning level defined by alarm thresholds.

Subsequently, the interval patient status is updated (Steps S362 to S370). More specifically, if the interval patient status is "warning", "warning" is maintained as it is (Step S362; Yes).

Then, when the interval patient status is other than "warning" and the current patient status is "warning", the interval patient status is set to "warning" (Step S362; No→Step S364; Yes→Step S366). That is, when the interval patient status is "caution" or "normal" and if the current patient status is "warning", the interval patient status is set to "warning".

When the interval patient status is "normal" and the current patient status is "caution", the interval patient status is set to "caution" (Step S362; No→Step S364; No→Step S368; Yes→Step S370). That is, when the interval patient status is "normal" and if the current patient status is "caution", the interval patient status is set to "caution". When the interval patient status is "caution" and the current patient status is "normal" or "caution", the state of "caution" is maintained as it is (Step S362; No→Step S364; No→Step S368; Yes→Step S370).

When the current patient status remains "normal" and the interval patient status is "normal", the interval patient status remains "normal" as it is (Step S362; No→Step S364; No→Step S368; No).

In this way, when the patient state is determined to be on a more critical state in the order of "normal"<"caution"<"warning", the interval patient status is updated to the more critical level. Once the state has reached the more critical level, the level is kept as it is until the status is cleared next (e.g., until the next login timing).

Then, based on the patient status (the interval patient status and the current patient status), the patient status distinctive display is updated (Step S372). Thus, the staff can easily confirm the current patient status and the worst state from the last logout time to the present.

Thereafter, until the login process is performed again, the process from Step S356 is repeated (Step S374; No→Step S356).

Now, the scheme of the operation of patient status distinctive display will be described with reference to FIG. 18. FIG. 18(a) shows an example of distinctive display of the patient status displayed on the screen. The distinctive display based on the interval patient status is given by M 102 while the distinctive display based on the current patient status is given by M 104. In the present embodiment, considering visibility, the distinctive display M104 is displayed larger, but the two displays may have the same size, or may be formed different in shape and position.

FIG. 18(b) shows an example of distinctive display of each patient status. For example, M110 shows normal, M112 shows caution, and M114 shows warning. Here, the display may be differentiated according to color, movement or shape. For example, in the case of color, normal may be indicated by "white", caution by "yellow" and warning by "red".

The operation will be briefly described with reference to FIGS. 18(c) to 18(e). Herein, it is assumed that the last logout time is t1 and the current point of time is t2.

In FIG. 18(c), though the patient status was "normal" at the time t1, the state once became worse to "warning", then transited to, and has stayed in, the "caution" state until t2.

In this case, the distinctive display M102 for the interval patient status is displayed with the "warning" state because the patient state became "warning" once after t1. Also, since the current status (at t2) is the caution level, the distinctive display M104 is displayed with the "caution" state.

In FIG. 18(d), the patient status was "caution" at time t1, but the current state (at t2) is "normal". In this case, the distinctive display M102 for the interval patient status is categorized and displayed with the "caution" state. On the other hand, since the patient state is "normal" at time t2, the distinctive display M 104 indicates "normal".

FIG. 18(e) is a diagram showing a case where the patient states was in the "normal" state at time t1, but changed to "caution" and "warning" from the middle of the interval. At the present (t2) as well, the patient state is at the "warning" level. In this case, the distinctive display M102 showing the interval patient status displays "warning", and the distinctive display M104 showing the current patient status also displays "warning".

Figure 18:
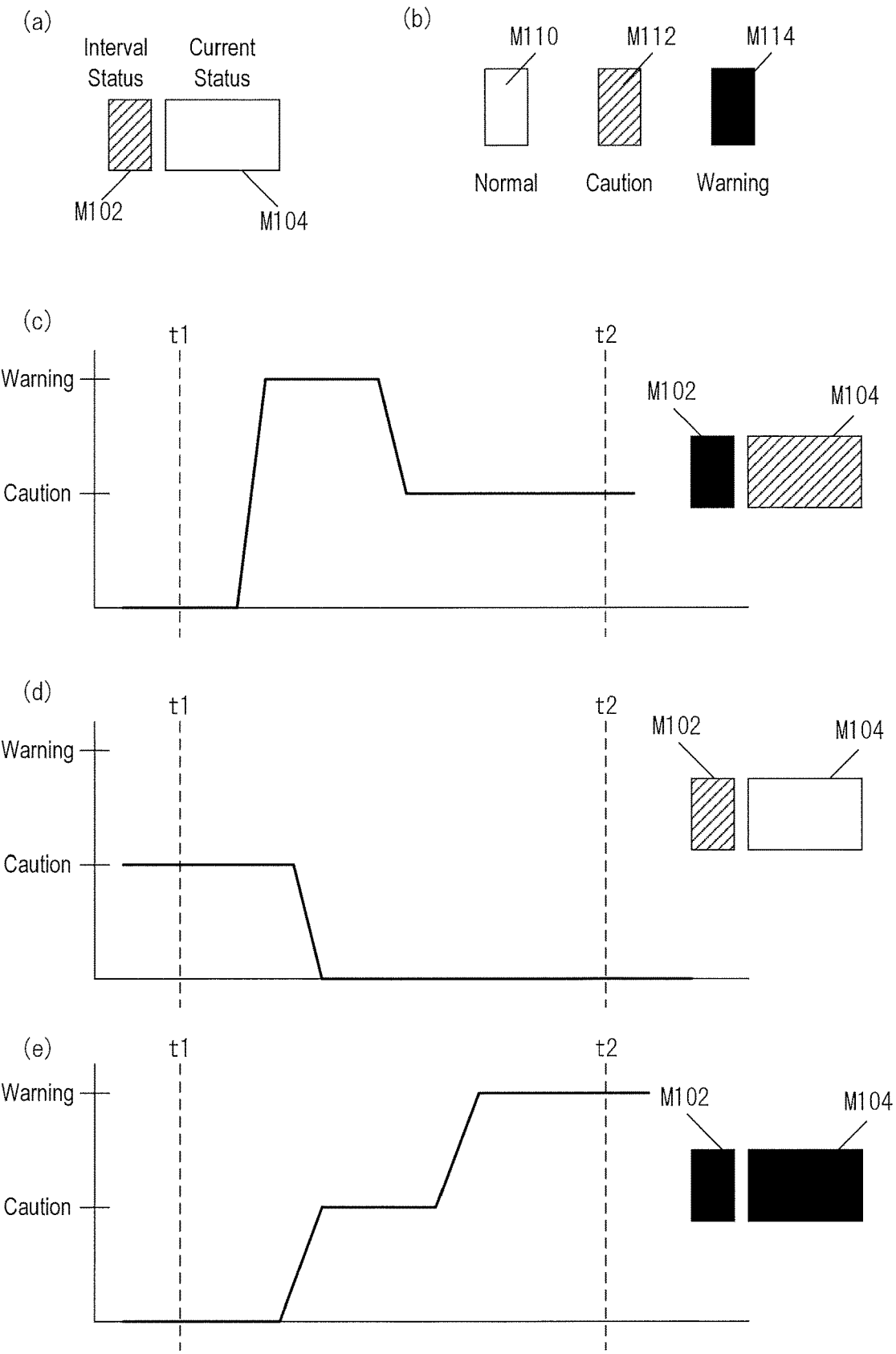
FIG. 18 illustrates a diagram for explaining an operation of a patient status distinctive display in the present embodiment.

Here in the description with FIG. 18, for description convenience, two kinds of distinctive displays are exemplified for explanation, but a plurality of distinctive displays may be provided adaptively. For example, not only the above-described distinctive display of the patient's upper body (whole), but distinctive display based only on continuous biological information may be performed. Further, special distinctive display may be performed in association with predetermined biological information (e.g., respiration rate and the like).

[4.3.3 Screen Examples]

Figure 19:
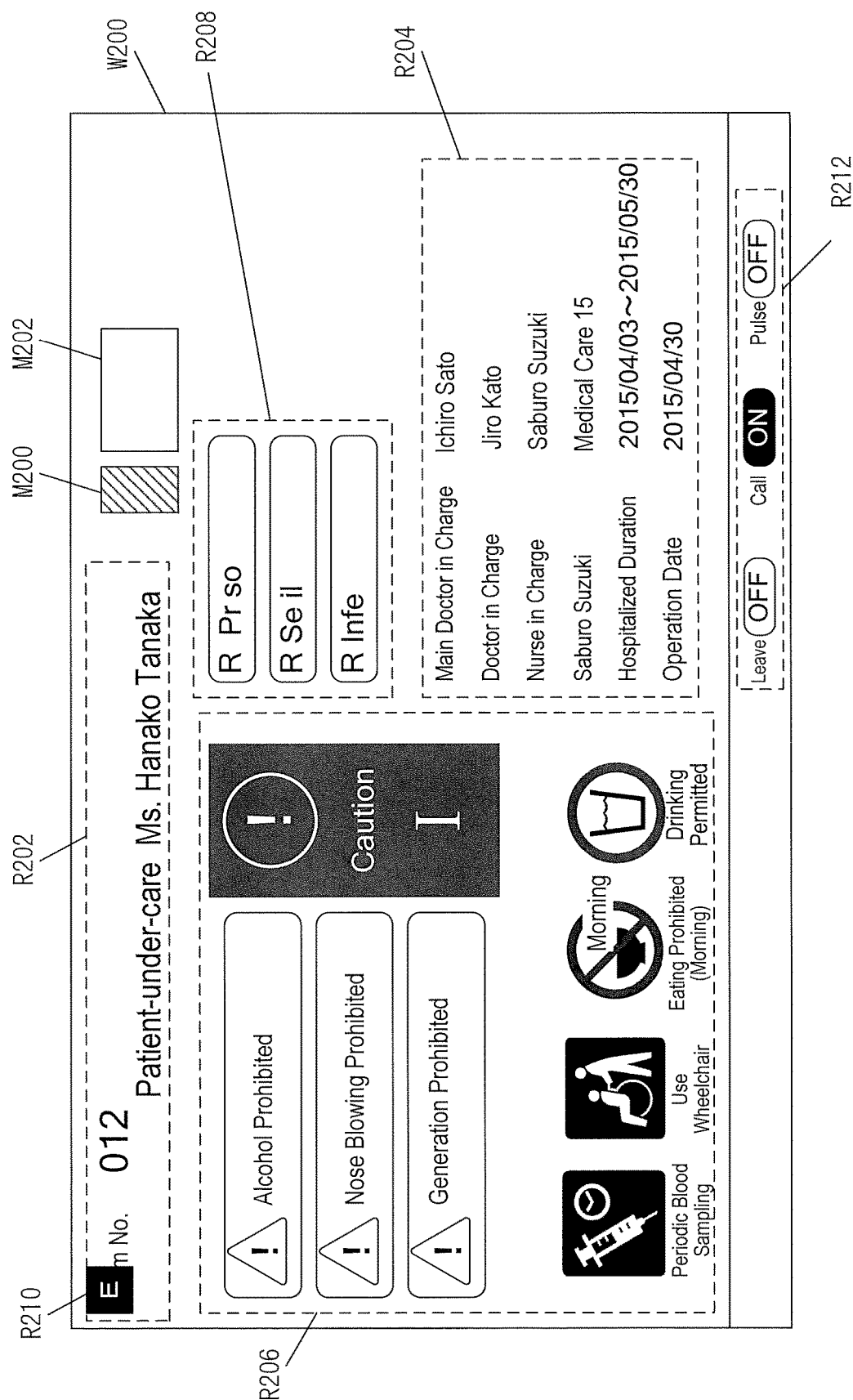
FIG. 19 illustrates a diagram for explaining a screen example as the operation example in the present embodiment.

Next, explanation on execution of this processing will be given using screen examples. FIG. 19 shows an example of a patient status display screen W200. Displayed in the regions R202 and R204 on the display screen W200 are the name of the patient, the name of the doctor in charge and the like as the name plate information. These items are appropriately selected from the patient information registered in the electronic medical record and displayed.

A region R206 is used as a pictogram region in which pictograms and the like are displayed. Further, displayed in a region R208 is special warning notice information from the caution information. The warning notice information is displayed in such a manner that only the experts such as medical staff and staff of nursing care facilities can understand.

R210 notifies that an error has occurred. Here, in order to display the error content, it is necessary to perform authentication to switch to another screen. This configuration makes it possible to prevent those other than the experts such as medical staff, caregivers and the like from checking the error.

Further, the operation and state of the state detection device 20 may be displayed on the display screen W200. For example, as shown in a region R212, the state may be displayed. The connection status of the sensor is also displayed. This makes it possible to grasp if the sensor is unconnected or unavailable at a glance.

In addition, patient status distinctive display is performed. In FIG. 19, the last patient status distinctive display is given in M200 and the current patient status distinctive display in M202. Various methods are available to perform patient status distinctive display. For example, an underline may be displayed under the patient name to perform distinctive display by the color or thickness of the line. Alternatively, a separate icon may be displayed.

Further, in the present embodiment, patient status distinctive display is performed on the entire biological information containing the continuous biological information and the measured biological information, but for example, display for the continuous biological information and that for the measured biological information may be separated. Further, biological information may be displayed such that only the respiration as biological information is displayed separately.

[4.4 Biological Information Display Process]

Subsequently, biological information display processing will be described. The biological information display processing is a process corresponding to P106 in FIG. 13. That is, it is the process of displaying biological information values based on the patient's electronic medical record data.

Figure 20:
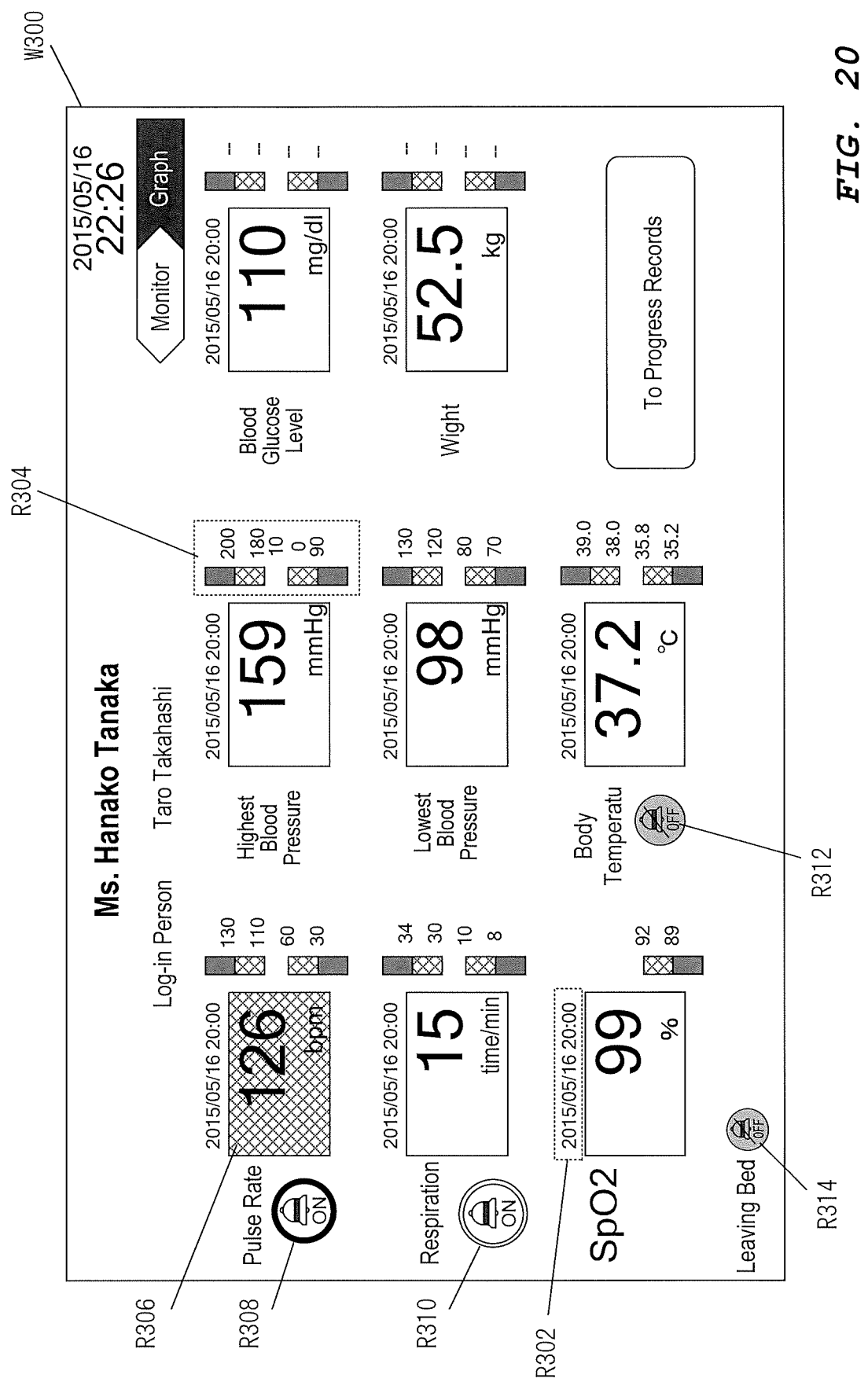
FIG. 20 illustrates a diagram for explaining a screen example as the operation example in the present embodiment.

FIG. 20 shows a display screen W300 as a screen example when this processing is executed. Displayed on the display screen W300 are biological information values for individual pieces of biological information. In a region R302, the date and time when the displayed biological information value was registered is displayed.

Further, beside the biological information value the alarm thresholds are displayed in a region R304 for easy viewing. That is, the alarm thresholds are displayed so as to clarify the caution level range and the warning level range.

Further, it is possible to configure the display such that the background is made distinctive when the displayed biological information value falls in the caution level range or the warning level range. For example, in R306, "126 bpm" is displayed as the pulse rate. Since this biological information value is contained in the caution level range, the background is displayed distinctively with a caution level color (e.g., yellow) or the like.

Further, a distinctive display may be performed in accordance with the biological information so as to show whether or not a notice should be given. For example, a display of R308 shows that a notification process should be performed when the biological information value of the pulse (pulse rate) falls in the warning level.

Also, R310 shows distinctively that notice processing should be performed when the biological information value of breathing (respiratory rate) exceeds the caution level.

Further, displays of R312 or R314 show that no notice processing should be performed. Though the display of FIG. 20 is a mere example, in this way it is possible to display whether or not to give notice based on biological information as necessary.

In addition, it is possible to provide a configuration such that the notification can be easily set by selecting (touching) the mark. For example, it is possible to have "notification off", "notice given above the caution level", or "notice give at warning level" set by touching the mark.

[4.5 Graph Display Process]

Next, graph display processing will be described. The graph display processing is a process executed in P108 of FIG. 13. That is, this is a process that displays the transition of the biological information registered in the electronic medical record as a graph.

Figure 21:
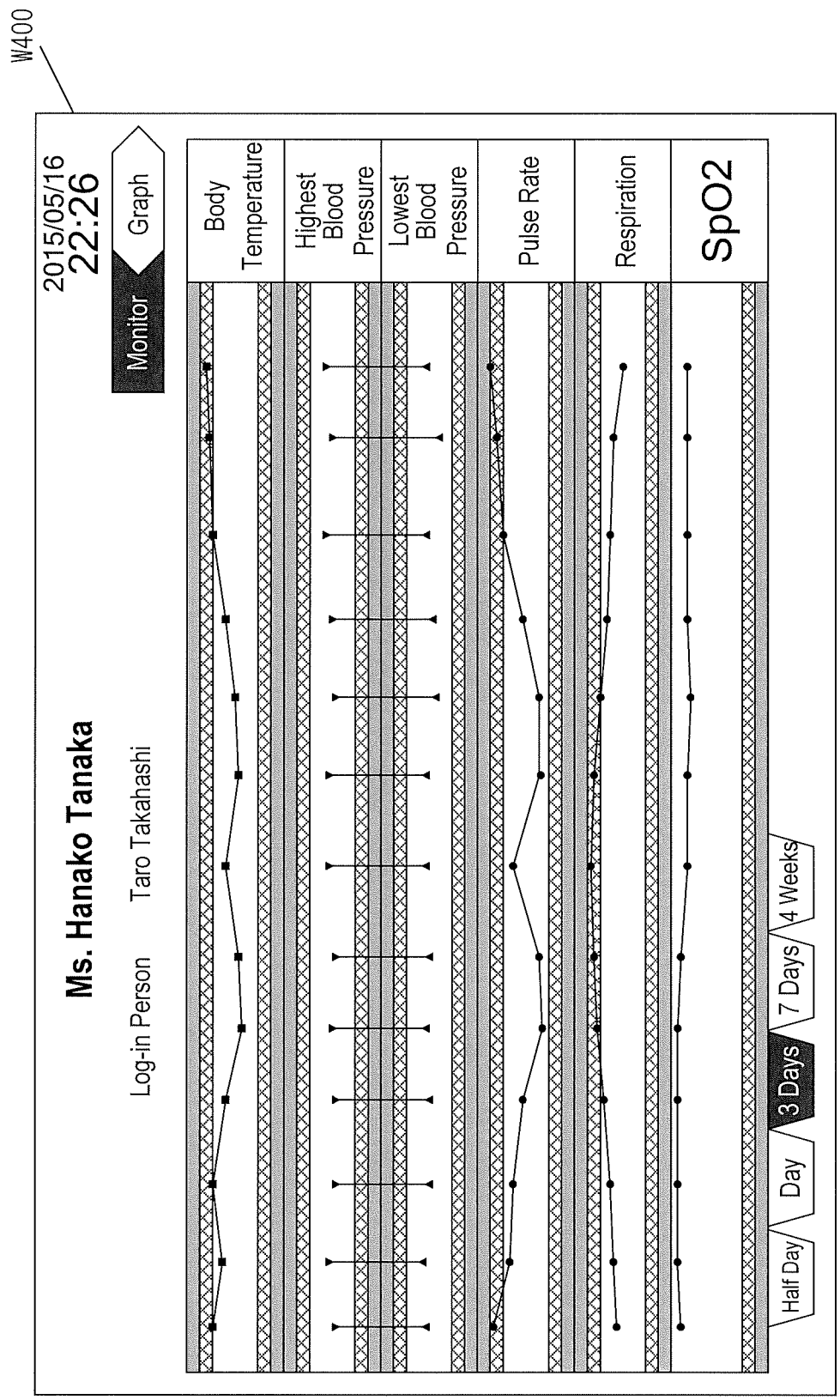
FIG. 21 illustrates a diagram for explaining a screen example as the operation example in the present embodiment.

FIG. 21 shows a display screen W400 as a screen example when this process is effected. The display screen W400 displays the transition of each biological information value. The ranges defined by the alarm thresholds are also displayed in the graph of each biological information. This enables easy grasp of each biological information if an anomaly arises.

Here, it is possible to provide such a configuration that when one of biological information is selected during display of this graph, the graph of the selected biological information alone is displayed.

[4.6 Electronic Medical Record Registering Process]

[4.6.1 Processing Flow]

Figure 22:
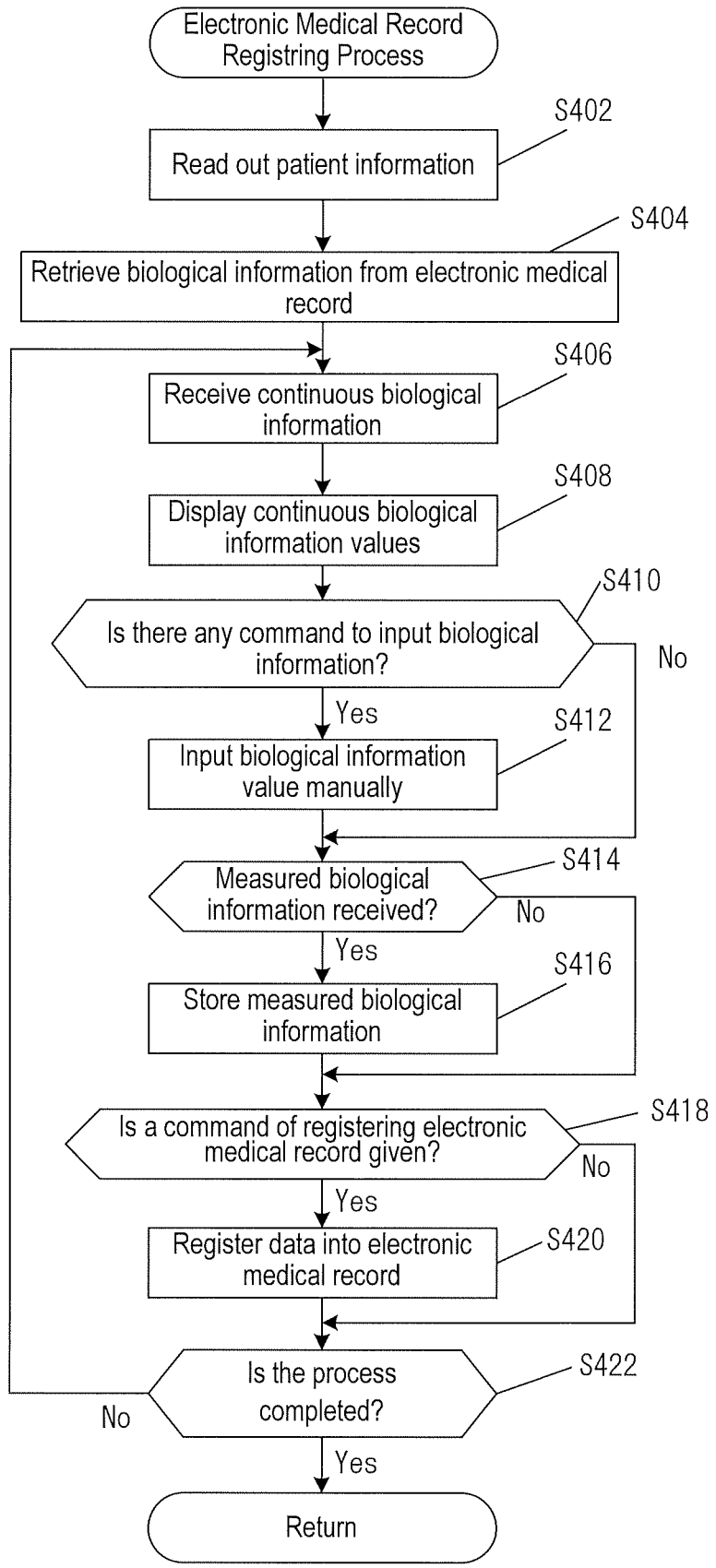
FIG. 22 illustrates a diagram for explaining an operation flow of an electronic medical record registering process in the present embodiment.

Next, an electronic medical record registering process for registering biological information in the electronic medical record will be described with reference to FIG. 22. The electronic medical record registering process is a process executed by the control unit 100 which reads out and executes the electronic medical record registering program 138 stored in the storage unit 110.

First, the patient information is read out (Step S402), so as to retrieve the biological information of the patient from the personal electronic medical record data 120 (Step S404). The kinds of biological information, the alarm thresholds and the like retrieved herein may be read out based on the patient basic information (e.g., patient ID) or the like, or may be set in common.

Subsequently, the continuous biological information is received from the state detection device 20 so that the values of the received biological information are displayed (Step S408). At this stage, when a command of entering biological information is given (Step S410: Yes), the biological information value is manually entered (Step S412).

At this time, when the biological information value falls within the range to output an alarm, distinctive display may be performed. For example, the background or characters, may be displayed with yellow when the biological information value falls in the caution level, and may be displayed with red when the value falls in the warning level. This arrangement enables the medical staff and the nursing care staff to grasp the fact that the biological information is currently causing a problem and also can alert the user to erroneous input and the like.

Further, as the continuous biological information to be displayed on the display screen, biological information (biological information values) that can be detected from the state detection device 20 may be updated as necessary, read out and displayed, or the biological information read out at a certain time may be displayed.

If the measured biological information is received from the other measuring device 60 (Step S414: Yes), the measured biological information is stored (Step S416). In this case, the currently displayed biological information value is updated and stored in the personal electronic medical record data 120.

Here, the time when the measured biological information is received from the other measuring device 60 is not limited. In this figure, the example is represented by Step S416, but the measured biological information that has been received previously may also be used. Also, the measured biological information may be arbitrarily stored in the personal electronic medical record data 120 (that is, the electronic medical record data 452). For example, if the value once measured is incorrect, the value is not stored and the value remeasured may be stored instead.

If a command of registering the electronic medical record is given (Step S418: Yes), the electronic medical record data 452 of the electronic medical record server 40 is registered (Step S420).

[4.6.2 Screen Example]

Figure 23:
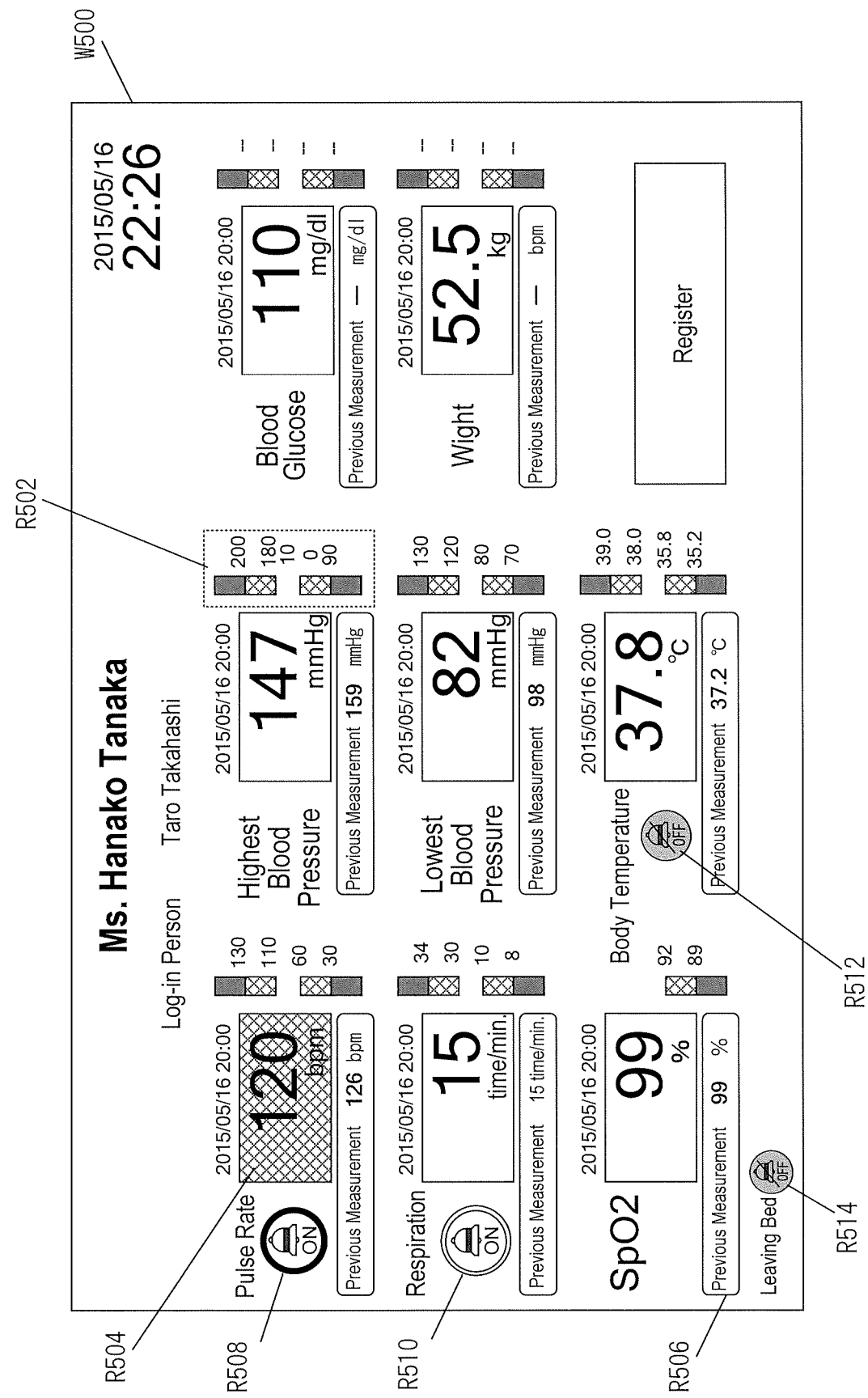
FIG. 23 illustrates a diagram for explaining a screen example as the operation example in the present embodiment.

FIG. 23 is a diagram showing a display screen W500 as an example when this process is executed. Displayed on the display screen W500 are individual biological information with the values thereof. As in FIG. 20, when the alarm thresholds are displayed in a region R502. When each biological information value falls in the caution level or the warning level, distinctive display is performed like R504.

Further, as shown in the region R506, the previously measured value may be displayed together. Over the biological information, the date and time when the last measurement was taken are also displayed. Thereby, the medical staff, the nursing staff and others can notice the change of the biological information value.

As to the displayed biological information values, for continuous biological information the values updated in real time may be displayed or the values at a certain point of time may be displayed. Alternatively, the values stored in the electronic medical record data (personal electronic medical record data 120 or electronic medical record data 452) may be displayed.

Then, selecting "register" on this screen makes it possible to register (store) the currently displayed biological information values as the electronic medical record data. By referring to the history, it is possible to check the past biological information values.

Further, whether or not a notice should be performed may be set in accordance with the biological information. For example, R308 is set such that a notification process should be performed when the biological information value of the pulse (pulse rate) falls in the warning level.

Also, R310 is set such that notification process should be performed when the biological information value of breathing (respiratory rate) exceeds the caution level. Further, displays of R312 or R314 are set such that no notification process should be performed.

Then, selecting "register" registers the data in the electronic medical record data and also updates the notice level table 126.

[4.7 Reminder Process]

Figure 24:
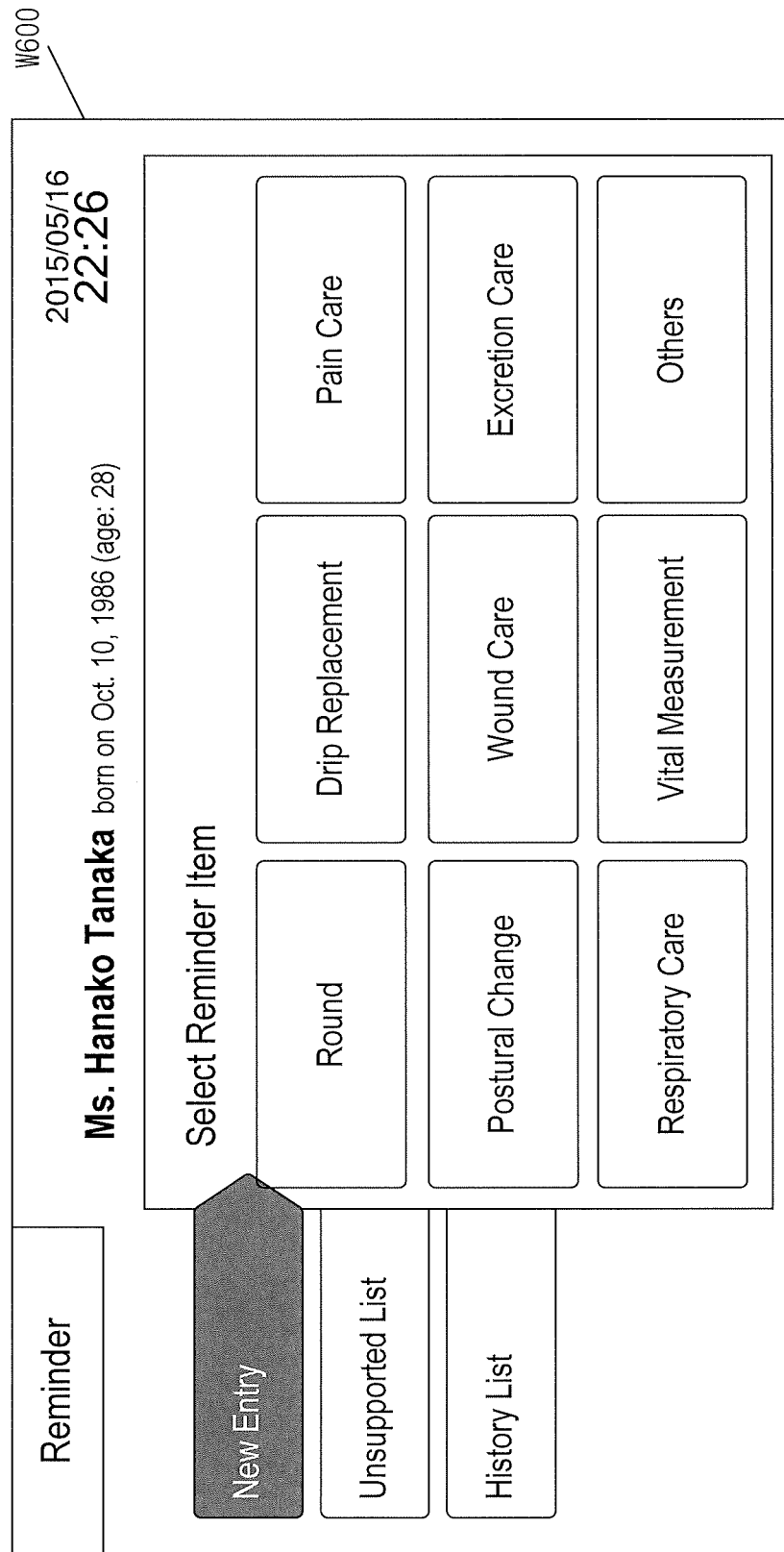
FIG. 24 illustrates a diagram for explaining a screen example as the operation example in the present embodiment.

Next, a reminder process will be described. The reminder process is a process which allows the staff and medical staff (nurses, etc.) to register what to do next as a reminder. For example, FIG. 24 shows an example of a display screen W600 displayed when this process is executed. By registering tasks to be displayed as various reminders, it is possible to display a reminder on the patient status display screen or the alarm display screen.

[4.8 Patient Information Display Process]

Next, a patient information display process will be described. The patient information display process is a process enables display of information on the patient. For example, it is possible to display, input and set basic information, medical care information, caution information pictogram and the like of the patient.

For example, FIG. 25 shows an example of a display screen W700 displayed when this process is effect. The display screen W700 reads out fundamental information (basic information) such as the name, gender and blood type of the patient from the electronic medical record and display them.

[4.9 Alarm Setting/History Process]

Next, an alarm setting/history process will be explained. This process is a process enabling the setting of each alarm threshold and the setting as to whether an alarm is permitted. It is also possible to check a history of alarms that occurred in the past. The alarm threshold is also used as a threshold at the time of notification.

Figure 26:
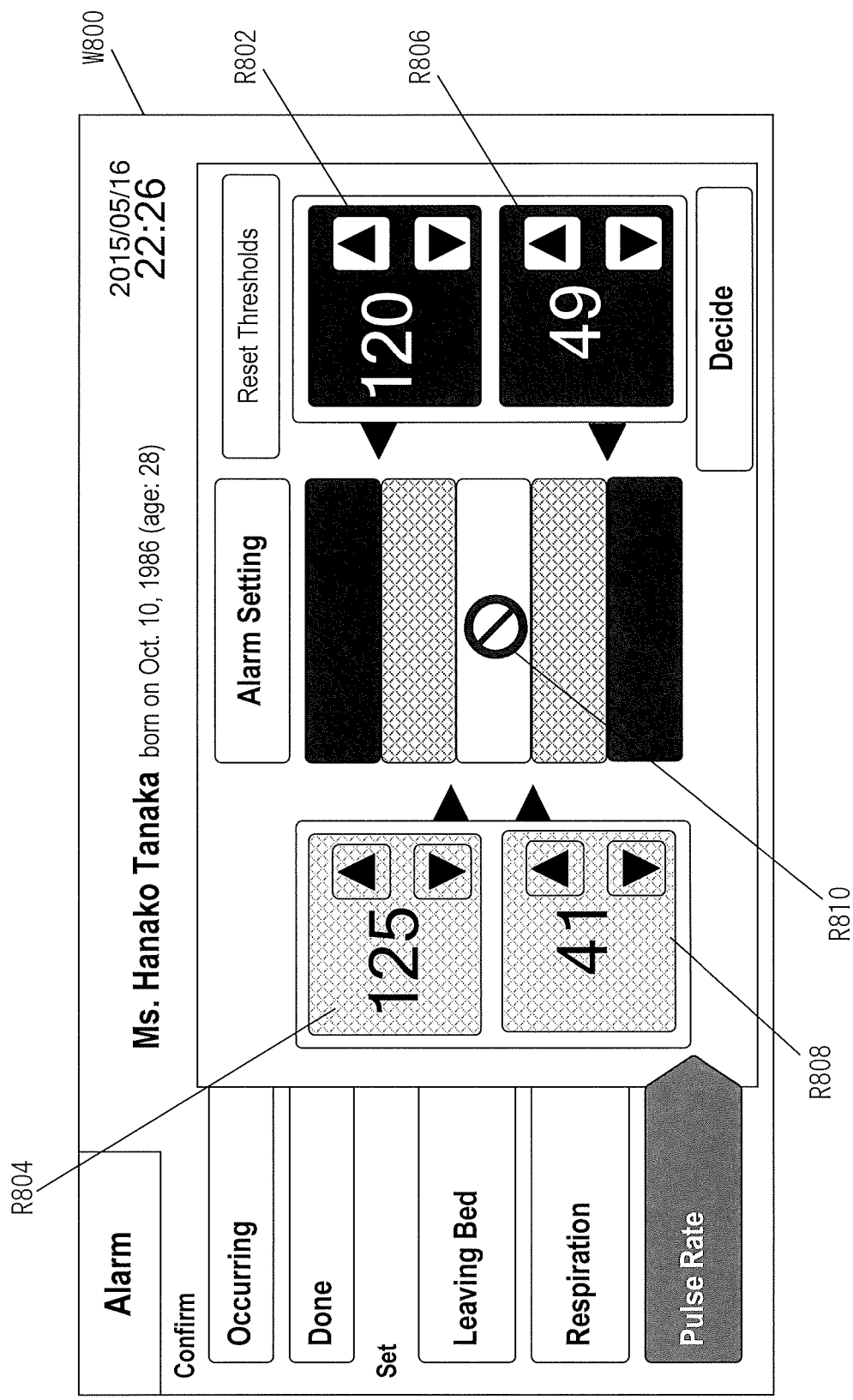
FIG. 26 illustrates a diagram for explaining a screen example as the operation example in the present embodiment.

FIG. 26 shows an example of a display screen W800 displayed when the alarm setting/history process is executed. In the display screen W800, alarm thresholds can be individually set. For example, as the upper alarm thresholds, the caution level threshold can be set in R804 and the warning level threshold can be set in R802.

Further, as the lower alarm threshold, the caution level threshold can be set in R808 and the warning level threshold can be set in R806.

In addition, it is possible to set whether or not to output an alarm when the information value falls in the range of caution level or warning level. For example, the setting in R810 indicates that no alarm (notice) is given.

Figure 27:
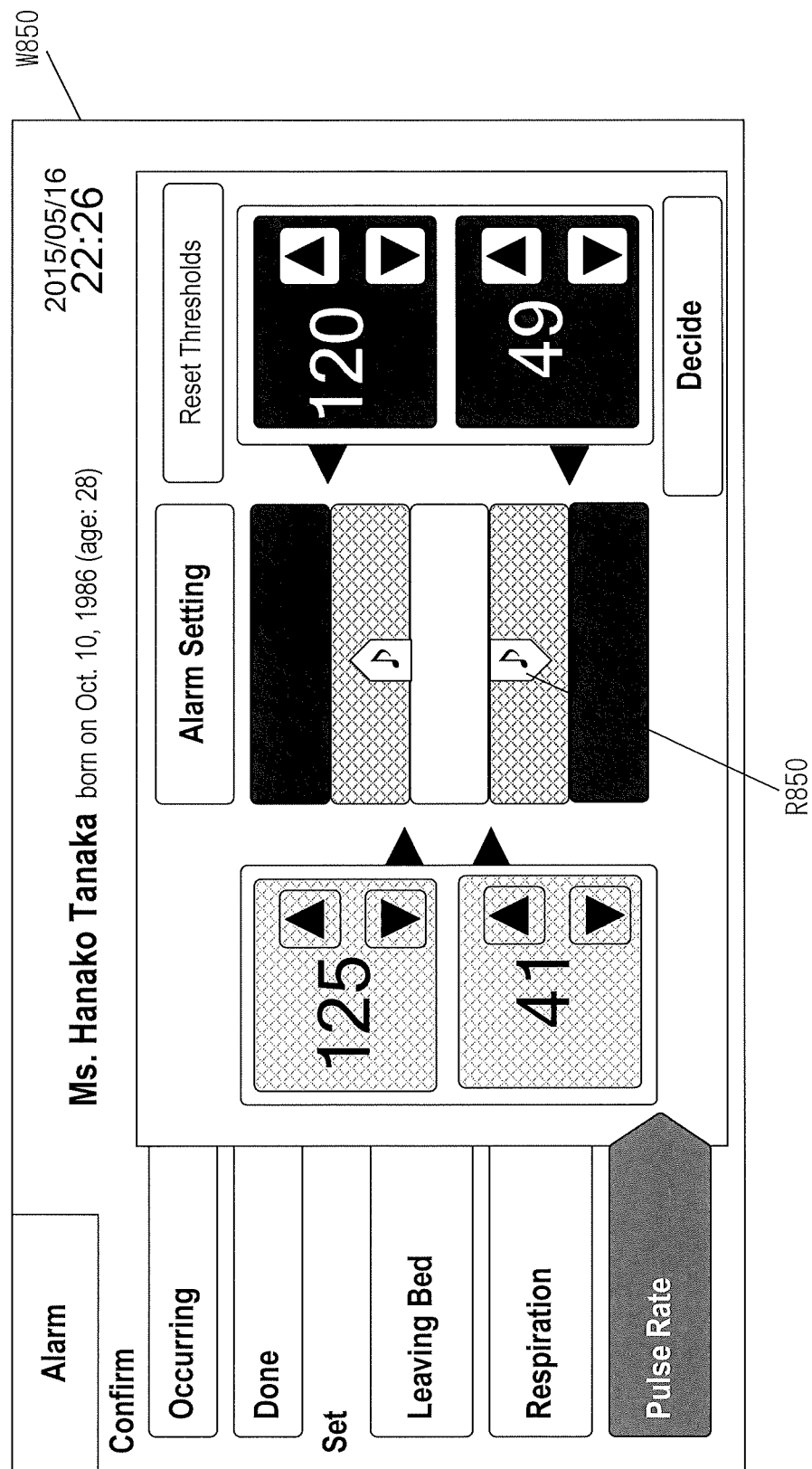
FIG. 27 illustrates a diagram for explaining the operation example in the present embodiment.

In a display screen W850 of FIG. 27, the setting in R850 indicates that an alarm is output when the information value falls in the caution level range. It should be noted that this setting may enable designation of, for example, sound alarm, light alarm or the like, and enables different alarm settings for the caution level and warning level.

5. Notification Process

Next, the notification process in this embodiment will be described. The notification process is an interrupt process for giving notice to predetermined notice destinations when one of the patient's biological information values reaches the level to give notice.

[5.1 First Notification Process]

Figure 28:
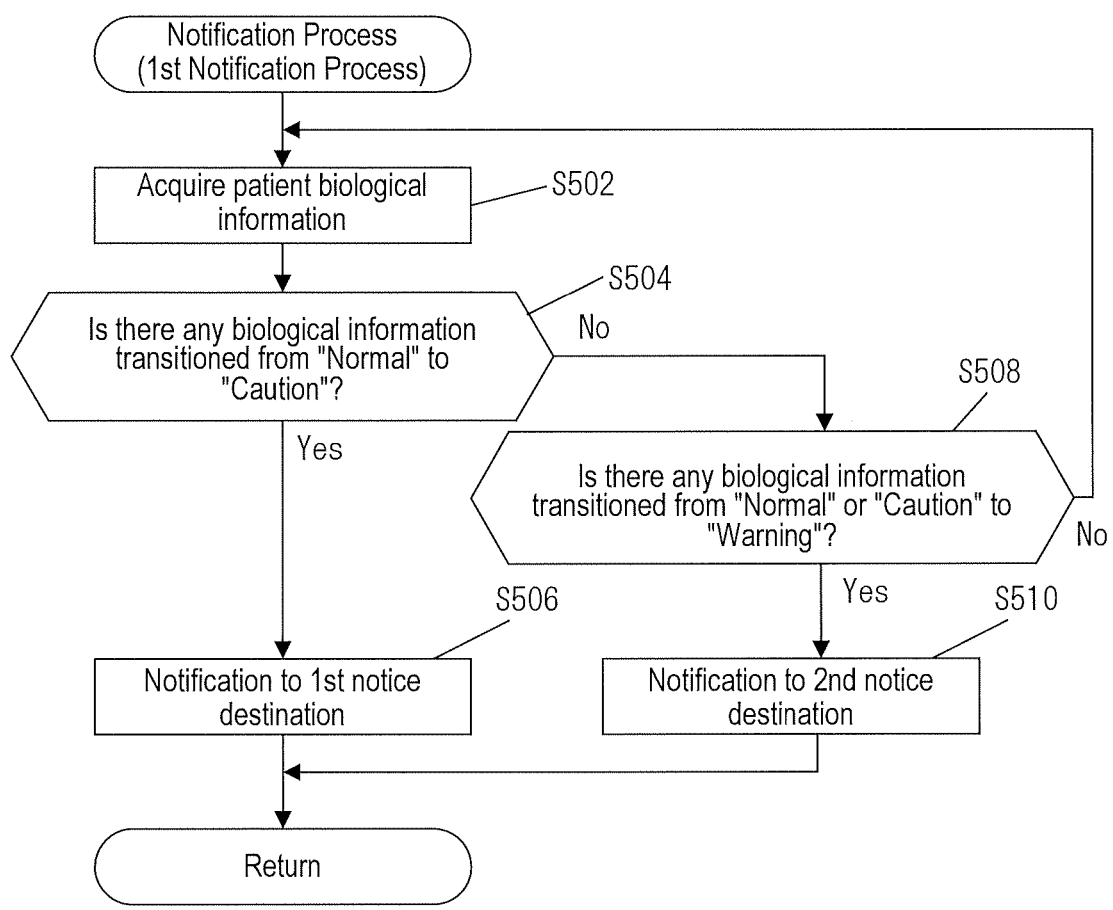
FIG. 28 illustrates a diagram for explaining an operation flow of a first notification process in the present embodiment.

First, as a notification process, the first notification process will be described with reference to FIG. 28. First, biological information of a patient is acquired (Step S502). Then, it is determined whether or not there are biological information which has transitioned from the normal level to the caution level (Step S504). That is, it is determined whether or not any of the biological information values of the biological information whose notice setting is designated with "caution" in the notice level table 126 is included in the caution level range.

Then, when the value of the biological information whose notice setting is designated with "caution" exceeds (falls below) the caution level threshold (falls within the caution level range), notice is performed to the first notice destination (Step S504; Yes→Step S506). Here, as an example, the first notice destination is a portable terminal device held by the nurse in charge and a terminal device in the nurse station, as shown in FIG. 9.

Also, when there is biological information that transits from the "normal" or "caution" state to the "warning" state, its notice is given to the second notice destination (Step S504; No→Step S508; Yes→Step S510). That is, when a biological information value of the biological information whose notice setting is set with "caution" or "warning" in the notice level table 126 exceeds (falls below) the warning level threshold (falls within the warning level range), notice is given to the second notice destination.

Here, examples of the second notice destination may include, as shown in FIG. 9, the portable terminal device of the nurse in charge, the terminal device at the nurse station, the portable terminal device possessed by the physician in charge.

When the notice setting is simply "ON", it is determined at Step S504 whether or not the state has been turned ON. For example, in a case where a notice is to be made when a leaving bed state is detected (leaving bed is "ON"), the first notice destination is notified when the leaving bed state is detected. In this case, the notice destination may be set to the second notice destination.

Figure 29:
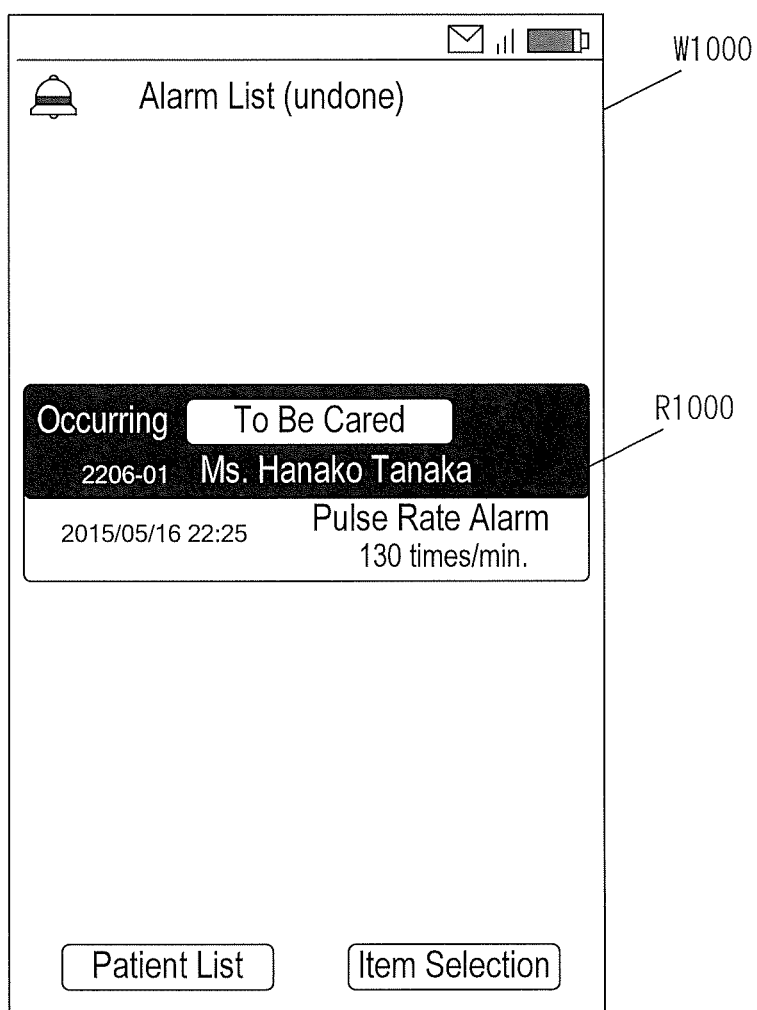
FIG. 29 illustrates a diagram for explaining the operation example in the present embodiment.

FIG. 29 shows an example of a display screen W1000 of the portable terminal device of the nurse in charge. The display screen shows an "alarm list", and alarms (notifications) of individual patients are displayed.

For example, in R1000, a notice is displayed together with patient's biological information. The display of this notice may be given, for example, as a pop-up on the operation screen, or by screen switching. In addition, for the display of the notice of R1000, for example, distinctive display may be made such as changing colors or icons between the caution level and the warning level.

Also, as in R1000, when the caution level (warning level) is reached, the biological information and the biological information value may be displayed together.

Figure 30:
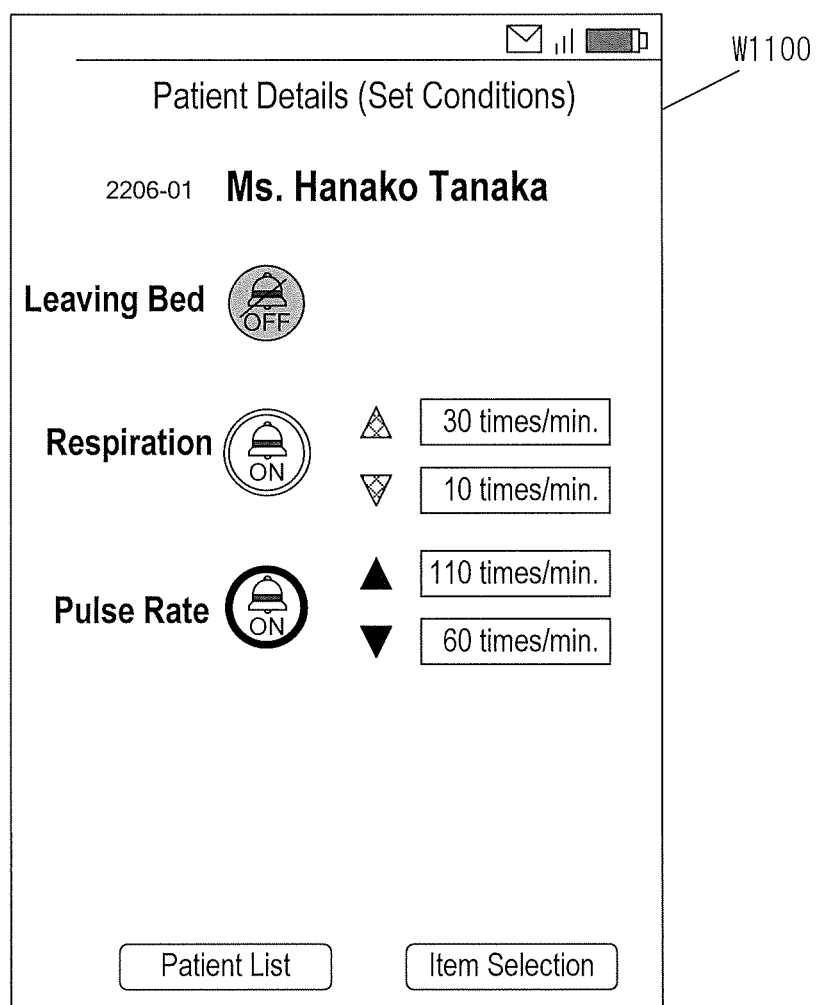
FIG. 30 illustrates a diagram for explaining the operation example in the present embodiment.

Further, these threshold levels may be configured to be set from the portable terminal device 55. For example, a screen with each information made to be settable may be displayed as in a display screen W1100 in FIG. 30, so that medical staff such as nurses, doctors and nursing care staff can set appropriately. As a result, it becomes possible to change necessary thresholds of a patient, so as to enable more appropriate notification.

Further, the threshold of notification may be changed depending on time and/or environment. For example, the threshold may be changed between daytime and nighttime, or the threshold may be changed according to the number of staff (e.g., depending on the number of patients whose notice is received).

[5.2 Second Notification Process]

Figure 31:
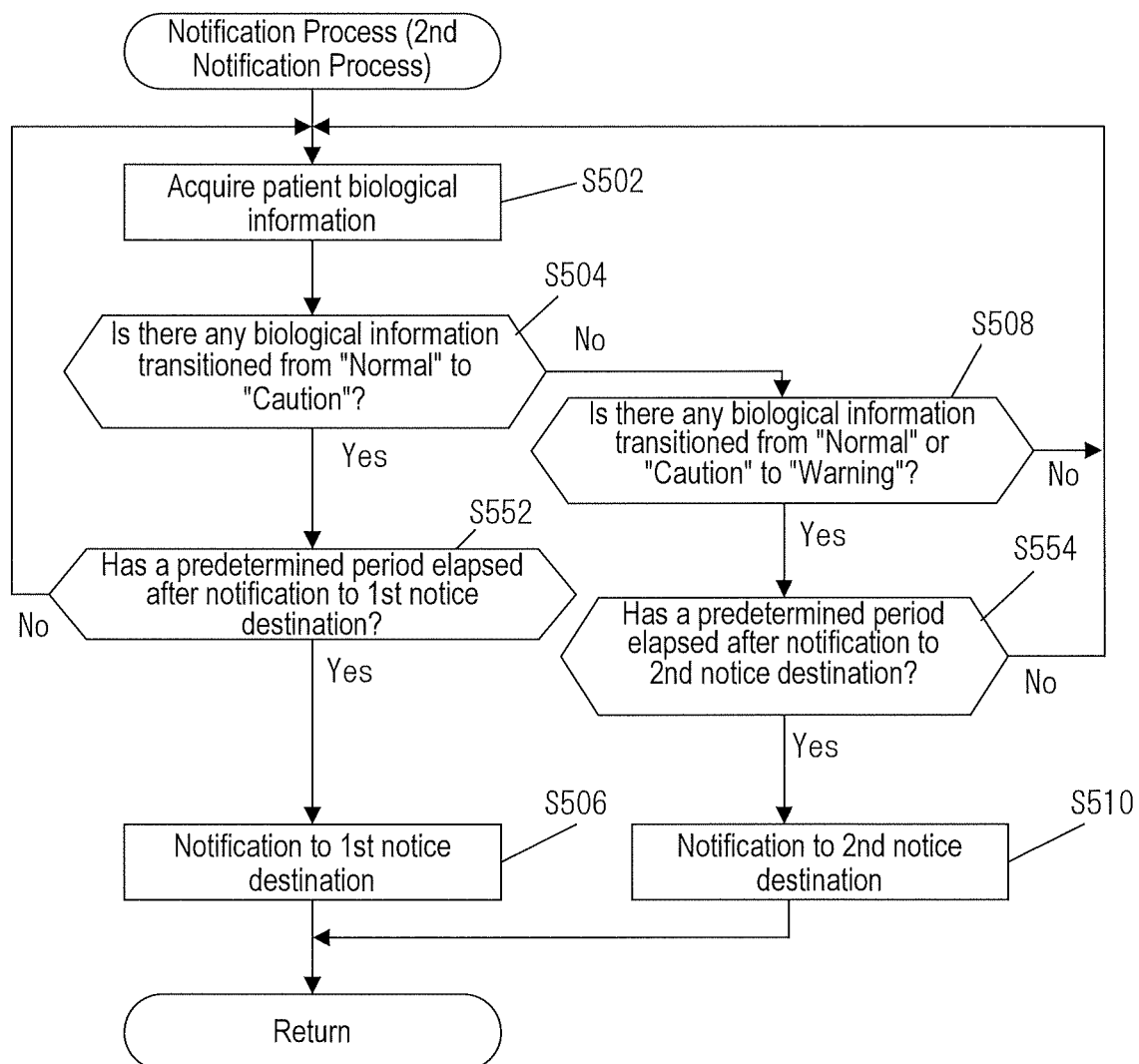
FIG. 31 illustrates a diagram for explaining an operation flow of a second notification process in the present embodiment.

Next, the second notification process will be described with reference to FIG. 31. In the second notification process, detailed description of the same procedures as those in the first notification process in FIG. 28 will be omitted by allotting the same reference numerals.

When, after acquiring the biological information of the patient, the value of the biological information for which the notice setting is "caution" exceeds (less than) the caution level threshold, notice is given to the first notice destination. At this occasion, it is determined whether or not a predetermined period of time has elapsed after making last notification to the first notice destination (Step S552). That is, when the predetermined time has not elapsed from the last notification, the status of the patient is regarded as remaining in the caution level, no notice is given (Step S552; No→Step S502). If the predetermined time has elapsed, notification is made to the first notice destination (Step S552; Yes→Step S506).

Similarly, when the value of the predetermined biological information exceeds (less than) the warning level threshold, notice is given to the second notice destination. At this occasion, it is determined whether or not a predetermined period of time has elapsed after making last notification to the second notice destination (Step S554). That is, when the predetermined time has not elapsed from the last notification, the status of the patient is regarded as remaining in the warning level, no notice is given (Step S554; No→Step S502). When the predetermined time has elapsed, notification is made to the second notice destination (Step S554; Yes→Step S510).

As described above, according to the second notification process, it is possible to prevent a plurality of notifications from being made when the biological information value varies.

[5.3 Third Notification Process]

Next, the third notification process will be described with reference to FIGS. 32 and 33. For example, as in this processing example, notification processing may be realized via the server 30.

Figure 32:
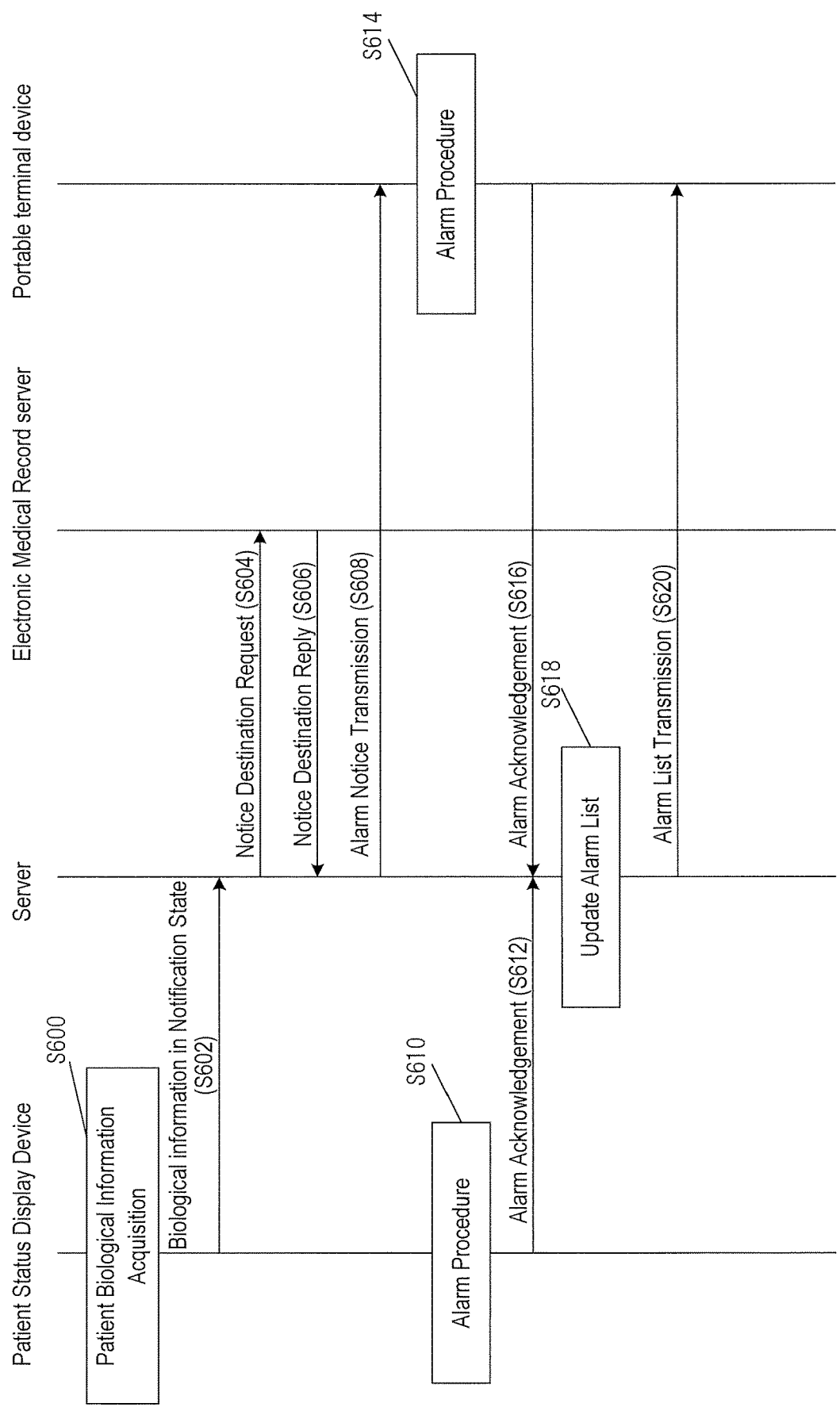
FIG. 32 illustrates a diagram for explaining an operation flow of a third notification process in the present embodiment.

Specifically, as shown in FIG. 32, the patient status display device 10 acquires the patient's biological information (S600). Of these, biological information being in a notification state (e.g., when the decision at Step S504 is "Yes" or when the decision at Step S508 is "Yes" at, in the above processing example), are transmitted to the server 30 (S602).

The server, based on the received notification state biological information, transmits a notice destination request to the electronic medical record server 40 in order to acquire the notice destination. The electronic medical record server 40 determines the notice destination from the information on the nurse in charge and the doctor in charge, registered in the electronic medical record and transmits a notice destination reply to the server 30 (S606).

Subsequently, the server 30 gives alarm notice to the terminal devices and portable terminal devices that are designated as the notice destination (S608). Then, when an alarm procedure is executed in the portable terminal device received the alarm notice (e.g., a confirmation button is touched by a nurse using the portable terminal device), the alarm procedure is executed (S614), and the alarm acknowledgment is transmitted to the server 30 (S616). Thus, the server 30 is able to manage what kind of alarm is occurring in each patient (in the notification state) and which staff member is attending. The thus managed information is updated as an alarm list (S618).

This alarm procedue may also be performed directly through the patient status display device 10 (S610), and an alarm acknowledgment reply may be transmitted from the patient status display device 10 to the server 30 (S612).

Then, the alarm list can be confirmed at each of terminal devices and portable terminal devices. That is, an alarm list is transmitted from the server 30 to the portable terminal devices (S620), whereby the list can be checked at each of the terminal devices and portable terminal devices.

Figure 33:
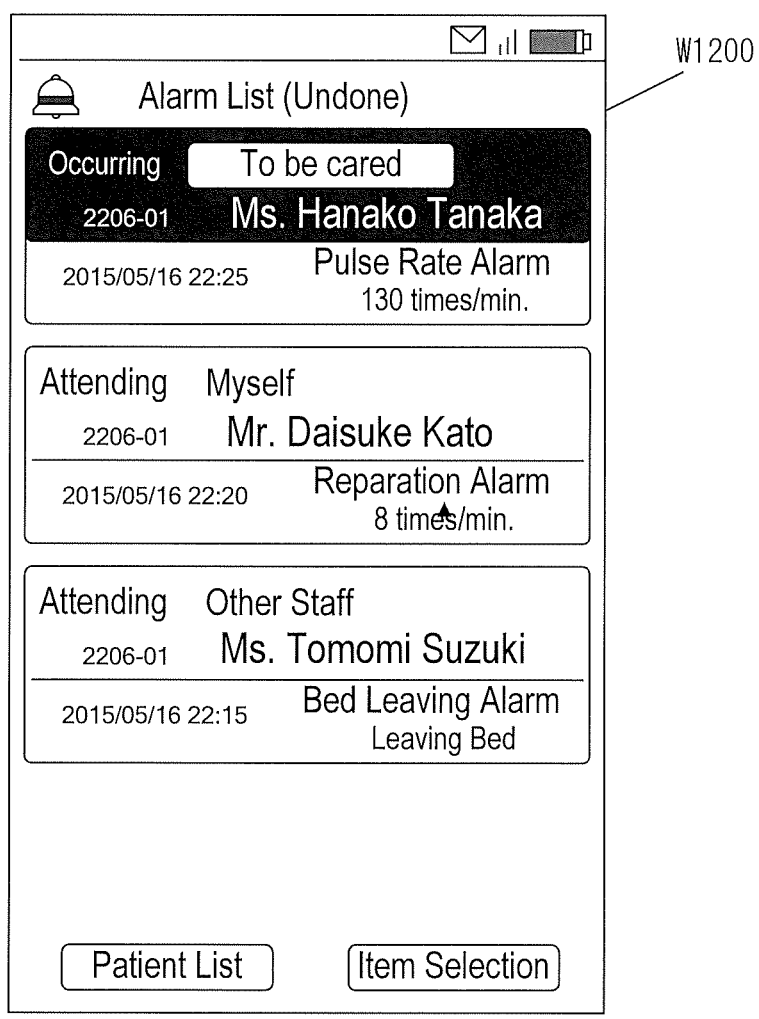
FIG. 33 illustrates a diagram for explaining the operation example in the present embodiment.

FIG. 33 shows an example of a display screen W1100 on which an alarm list is displayed. Here, a list of patients with an alarm occurring currently or an alarm having occurred in the past is displayed. The list also displays whether each patient is currently attended or unattended. The list further displays which staff member is attending and what state of the biological information (value) in the alarming mode is in, on the display screen.

Though the sequence diagram in FIG. 32 is an example, it is thus possible to execute the process in the server 30 and receive the result at the patient status display device 10.

That is, various programs (e.g., the main program 132, the alarm program 134, the patient status display program 136, the electronic medical record registering program 138, the notification program 140) are executed on the server 30 as necessary. The patient status display device 10 transmits biological information to the server 30 while the server 30 is accessed by, for example, a WEB browser or a dedicated application, whereby it is possible to realize the same procedures.

In addition, though the patient status display device 10 is also configured separately of the display terminal 1000 and the connection device 2000, these components may be integrated and presented as a dedicated patient status display device 10.

Separation of the display terminal 1000 and the connection device 2000 produces such an advantage as to enable use of a tablet terminal satisfying predetermined conditions as the display terminal 1000. Thus, it is possible to consider use of commercially available tablet terminals, computers and smartphones.

Further, the patient status display device 10 is typically installed near the bed, whereas the same screen can be displayed on the terminal device 50 and the portable terminal device 55. For example, checking patient information with the portable terminal device 55 even while the nurse is rounding and use of the terminal device 50 at the nurse station, makes it possible to manage the patient with other patients in a unified manner.

Moreover, even in medical treatment or during examination, biological information can be updated at any time through the terminal device 50, it is hence possible to improve the handling of electronic medical records.

6. Modified Example

Though the embodiment of the present invention has been described in detail with reference to the drawings, the specific configuration is not limited to this embodiment, and designs and others that do not depart from the gist of this invention should also included in the scope of claims.

The programs to run in each device of the embodiment may be programs (programs that make a computer function) for controlling a CPU or the like so as to realize the functions of the embodiment described above. The information to be handled in these devices is temporarily stored in temporary memory (e.g., RAM) at the time of processing, then is stored into storages such as various kinds of ROM and/or HDDs, and is read out, modified and written in by the CPU, as necessary.

Herein, the recording medium for storing the program may be any of semiconductor mediums (e.g., ROM, non-volatile memory card, etc.), optical recording mediums/ magneto optical mediums (e.g., DVD (Digital Versatile Disc), MO (Magneto Optical Disc), CD (Compact Disc), BD and the like), magnetic recording mediums (e.g., magnetic tape, flexible disc, etc.), and the like. Further, the functions of the above-described embodiments are not only realized by executing the loaded program, but the functions of the present invention may also be realized by processing in cooperation with an operating system, another application program or the like, based on the instructions of the running program.

DESCRIPTION OF REFERENCE NUMERALS

To put the product on the market, the program may be stored on a removable storing medium to put the program on the market, or may be transferred to a server computer connected to a network such as the Internet or the like. In this case, it goes without saying that the storage device of the server computer is also included in the present invention.

1 patient notification system
3 bed
5 mattress
10 patient status display device
1000 display terminal
100 control unit
110 storage unit
112 biological information
114 continuous biological information
116 measured biological information
120 personal electronic medical record data
122 alarm threshold table
124 patient status distinctive information
126 notice level table
132 main program
134 alarm program
136 patient status display program
138 electronic medical record registering program
140 notification program
150 device communicator
160 operation unit
170 display unit
180 LAN communicator
2000 connection device
200 control unit
210 storage unit
220 communicator
230 interface unit
240 wireless communicator
250 device communicator
260 notifying unit
20 state detection device
30 server
40 electronic medical record server
400 control unit
410 communicator
450 storage unit
452 electronic medical record data
50 terminal device
55 portable terminal device
60 measuring device
65 authentication card

The invention claimed is:

1. A system for monitoring a state, comprising:
a plurality of terminal devices including a first terminal device and a second terminal device; and
a controller configured to:
activate a first alarm to the first terminal device if a first state is satisfied with a first alarm condition; and
activate a second alarm to the second terminal device if the first state is satisfied with a second alarm condition, the second alarm condition being different from the first alarm condition, the first state being a state of a user,
wherein a first method to activate the first alarm is different from a second method to activate the second alarm,
wherein the first terminal device is configured to display both a current status of the user and a historical status of the user, the historical status indicating only a worst status of the user from a first time to a current time in a patient status display screen,
wherein the first terminal device is configured to display a staff screen after performing authentication processing in the patient status display screen, and
wherein the first terminal device is configured to display a graph display screen which is capable of displaying the history of the state of the user or a registration screen which is capable of registering the state of the user in the electronic medical record through the staff screen from the patient status display screen.

2. The system according to the claim 1, wherein the first method includes a method to display the first alarm in the first terminal device, and the second method includes a method to make sound or voice as the second alarm.

3. The system according to the claim 1, wherein the second terminal device is capable of displaying an icon to determine whether caregiver who holds the second terminal device will deal with the second alarm if the second alarm is activated.

4. The system according to the claim 1, further comprising at least one sensor configured to automatically and continuously acquire biological data from the user, and
wherein the controller is configured to:
receive biological data of the user;
compare the received biological data with at least one of threshold values;

activate the first alarm to the first terminal device if the first state is satisfied with the first alarm condition, the first state being the state of the user.

5. The system according to the claim 4, wherein the first method includes a method to display the first alarm in the first terminal device, and the second method includes a method to make sound or voice as the second alarm.

6. The system according to the claim 4, wherein the one or more threshold values compared with the received biological data are selected based on an associated patient identifier, a type of the received biological data and a notice setting in an alarm notice level table.

7. The system according to the claim 4, wherein the controller is configured to determine the received biological data is satisfied with a first alarm condition if the received biological data is determined to be outside of a first range, the controller is configured to determine the received biological data is satisfied with a second alarm condition if the received biological data is determined to be outside of a second range, and the second range includes the first range.

8. The system according to the claim 1, wherein the controller is configured to re-activate the first alarm to the first terminal device if a first state is satisfied with a first alarm condition and a first period have elapsed from activating the first alarm.

9. The system according to the claim 8, wherein the controller is configured to re-activate the second alarm to the second terminal device if a first state is satisfied with a second alarm condition and a second period have elapsed from activating the second alarm.

10. The system according to the claim 1, wherein the first or second terminal device is capable of displaying status about the first alarm and the second alarm, the status including a name of the user, a reason why the first alarm or the second alarm is activated, and a name of caregiver who will deal with the first alarm or the second alarm.

11. The system according to the claim 1, wherein the first or second terminal device is capable of changing the first alarm condition or the second alarm condition.

12. The system according to the claim 11, wherein the second alarm condition is related to biological data and a status whether the user is staying on a bed.

* * * * *